(12) United States Patent
McRoberts et al.

(10) Patent No.: US 10,154,019 B2
(45) Date of Patent: Dec. 11, 2018

(54) END-TO-END TRUSTED COMMUNICATIONS INFRASTRUCTURE

(71) Applicant: Sprint Communications Company L.P., Overland Park, KS (US)

(72) Inventors: Leo Michael McRoberts, Overland Park, KS (US); Lyle W. Paczkowski, Mission Hills, KS (US); David E. Rondeau, Olathe, KS (US)

(73) Assignee: Sprint Communications Company L.P., Overland Park, KS (US)

( * ) Notice: Subject to any disclaimer, the term of this patent is extended or adjusted under 35 U.S.C. 154(b) by 498 days.

(21) Appl. No.: 15/005,123

(22) Filed: Jan. 25, 2016

(65) Prior Publication Data

US 2016/0142396 A1    May 19, 2016

Related U.S. Application Data

(63) Continuation of application No. 13/532,588, filed on Jun. 25, 2012, now Pat. No. 9,282,898.

(51) Int. Cl.
| | |
|---|---|
| *H04L 29/06* | (2006.01) |
| *H04W 12/06* | (2009.01) |
| *H04L 29/08* | (2006.01) |
| *G06F 21/32* | (2013.01) |
| *A61B 5/00* | (2006.01) |

(Continued)

(52) U.S. Cl.
CPC ............ *H04L 63/08* (2013.01); *A61B 5/0022* (2013.01); *G06F 19/00* (2013.01); *G06F 21/32* (2013.01); *G16H 40/67* (2018.01); *H04L 67/141* (2013.01); *H04W 12/06* (2013.01); *A61B 5/01* (2013.01); *A61B 5/021* (2013.01); *A61B 5/024* (2013.01); *A61B 5/145* (2013.01); *A61B 5/1455* (2013.01); *H04L 63/105* (2013.01)

(58) Field of Classification Search
None
See application file for complete search history.

(56) References Cited

U.S. PATENT DOCUMENTS

| | | |
|---|---|---|
| 5,303,378 A | 4/1994 | Cohen |
| 5,321,735 A | 6/1994 | Breeden et al. |

(Continued)

FOREIGN PATENT DOCUMENTS

| | | |
|---|---|---|
| EP | 1933252 A1 | 6/2008 |
| GB | 2456754 A | 7/2009 |

(Continued)

OTHER PUBLICATIONS

Examiner's Answer dated Nov. 16, 2016, U.S. Appl. No. 14/632,850, filed Feb. 26, 2015.

(Continued)

*Primary Examiner* — Michael Tomaszewski

(57) ABSTRACT

A method establishing a trusted end-to-end communication link is disclosed. The method comprises executing a communication application in a trusted security zone of a mobile access terminal. The method also comprises sending a message from the mobile access terminal to a trusted communication application executing in a trusted security zone of a trusted enterprise edge node. The method further comprises sending the message from the trusted enterprise edge node to a trusted cloudlet executing in a trusted security zone of a cloud based server.

20 Claims, 11 Drawing Sheets

(51) Int. Cl.
*G06F 19/00* (2018.01)
*G16H 40/67* (2018.01)
*A61B 5/01* (2006.01)
*A61B 5/021* (2006.01)
*A61B 5/024* (2006.01)
*A61B 5/145* (2006.01)
*A61B 5/1455* (2006.01)

(56) References Cited

U.S. PATENT DOCUMENTS

| | | |
|---|---|---|
| 5,764,889 A | 6/1998 | Ault et al. |
| 5,796,952 A | 8/1998 | Davis et al. |
| 5,825,876 A | 10/1998 | Peterson, Jr. |
| 6,131,024 A | 10/2000 | Boltz |
| 6,177,860 B1 | 1/2001 | Cromer et al. |
| 6,219,712 B1 | 4/2001 | Mann et al. |
| 6,222,463 B1 | 4/2001 | Rai |
| 6,363,150 B1 | 3/2002 | Bhagavath et al. |
| 6,389,403 B1 | 5/2002 | Dorak, Jr. |
| 6,434,561 B1 | 8/2002 | Durst, Jr. et al. |
| 6,477,180 B1 | 11/2002 | Aggarwal et al. |
| 6,507,869 B1 | 1/2003 | Franke et al. |
| 6,507,904 B1 | 1/2003 | Ellison et al. |
| 6,614,893 B1 | 9/2003 | Paiz |
| 6,651,171 B1 | 11/2003 | England et al. |
| 6,668,322 B1 | 12/2003 | Wood et al. |
| 6,691,230 B1 | 2/2004 | Bardon |
| 6,754,784 B1 | 6/2004 | North et al. |
| 6,823,454 B1 | 11/2004 | Hind et al. |
| 6,824,064 B2 | 11/2004 | Guthery et al. |
| 6,895,234 B1 | 5/2005 | Laursen et al. |
| 7,023,979 B1 | 4/2006 | Wu et al. |
| 7,043,241 B1 | 5/2006 | Sladek et al. |
| 7,069,234 B1 | 6/2006 | Cornelius et al. |
| 7,127,541 B2 | 10/2006 | Govindarajulu et al. |
| 7,366,806 B2 | 4/2008 | Milenkovic et al. |
| 7,386,275 B2 | 6/2008 | Pirzada et al. |
| 7,387,240 B2 | 6/2008 | Ziegler |
| 7,519,824 B1 | 4/2009 | Peyravian et al. |
| 7,552,467 B2 | 6/2009 | Lindsay |
| 7,571,364 B2 | 8/2009 | Whetsel |
| 7,574,382 B1 | 8/2009 | Hubert |
| 7,650,645 B1 | 1/2010 | Langendorf et al. |
| 7,716,720 B1 | 5/2010 | Marek et al. |
| 7,761,558 B1 | 7/2010 | Jindal et al. |
| 7,849,309 B1 | 12/2010 | Brown |
| 7,873,837 B1 | 1/2011 | Lee et al. |
| 7,895,642 B1 | 2/2011 | Larson et al. |
| 7,921,303 B2 | 4/2011 | Mauro, II |
| 8,060,449 B1 | 11/2011 | Zhu |
| 8,073,428 B2 | 12/2011 | Khetawat et al. |
| 8,086,238 B1 | 12/2011 | Kosar |
| 8,112,794 B2 * | 2/2012 | Little .................. H04L 63/0853 380/270 |
| 8,155,642 B2 | 4/2012 | Russell |
| 8,190,919 B2 | 5/2012 | Natarajan et al. |
| 8,204,480 B1 | 6/2012 | Lindteigen et al. |
| 8,238,823 B2 | 8/2012 | Maugars et al. |
| 8,271,336 B2 | 9/2012 | Mikurak |
| 8,295,811 B1 | 10/2012 | Gailloux et al. |
| 8,298,295 B2 | 10/2012 | Aissi et al. |
| 8,316,237 B1 | 11/2012 | Felsher et al. |
| 8,332,895 B2 | 12/2012 | Nathan et al. |
| 8,332,953 B2 | 12/2012 | Lemieux et al. |
| 8,402,543 B1 | 3/2013 | Ranjan et al. |
| 8,413,229 B2 | 4/2013 | Mullick et al. |
| 8,429,409 B1 | 4/2013 | Wall et al. |
| 8,442,588 B2 | 5/2013 | Sims et al. |
| 8,443,420 B2 | 5/2013 | Brown et al. |
| 8,447,983 B1 | 5/2013 | Beck et al. |
| 8,494,576 B1 | 7/2013 | Bye et al. |
| 8,498,572 B1 | 7/2013 | Schooley et al. |
| 8,504,097 B1 | 8/2013 | Cope et al. |
| 8,542,833 B2 | 9/2013 | Devol et al. |
| 8,566,183 B1 | 10/2013 | Bonar et al. |
| 8,588,749 B1 | 11/2013 | Sadhvani et al. |
| 8,590,012 B2 | 11/2013 | Roy et al. |
| 8,631,247 B2 | 1/2014 | O'Loughlin et al. |
| 8,632,000 B2 | 1/2014 | Laracey |
| 8,649,770 B1 | 2/2014 | Cope et al. |
| 8,650,492 B1 | 2/2014 | Mui et al. |
| 8,661,119 B1 | 2/2014 | Jindal et al. |
| 8,667,607 B2 | 3/2014 | Paczkowski et al. |
| 8,681,969 B1 | 3/2014 | Rodde et al. |
| 8,699,998 B2 | 4/2014 | Sprigg et al. |
| 8,707,056 B2 | 4/2014 | Felton |
| 8,712,407 B1 | 4/2014 | Cope et al. |
| 8,718,554 B2 | 5/2014 | Abel |
| 8,719,586 B1 | 5/2014 | Paleja et al. |
| 8,726,343 B1 | 5/2014 | Borzycki et al. |
| 8,738,333 B1 | 5/2014 | Behera et al. |
| 8,750,839 B1 | 6/2014 | Paczkowski et al. |
| 8,752,140 B1 | 6/2014 | Paczkowski et al. |
| 8,762,298 B1 | 6/2014 | Ranjan et al. |
| 8,787,873 B1 | 7/2014 | Hitt et al. |
| 8,793,808 B2 | 7/2014 | Boccon-Gibod |
| 8,797,875 B2 | 8/2014 | Garcia Martin et al. |
| 8,811,971 B2 | 8/2014 | Corda et al. |
| 8,826,015 B2 | 9/2014 | Lakshminarayanan et al. |
| 8,831,998 B1 | 9/2014 | Cramer et al. |
| 8,839,460 B2 | 9/2014 | Shirlen et al. |
| 8,850,568 B2 | 9/2014 | Shirlen et al. |
| 8,856,600 B2 | 10/2014 | Zadigian et al. |
| 8,862,181 B1 | 10/2014 | Cope et al. |
| 8,863,252 B1 | 10/2014 | Katzer et al. |
| 8,868,898 B1 | 10/2014 | Van Hoof |
| 8,881,977 B1 | 11/2014 | Paczkowski et al. |
| 8,886,925 B2 | 11/2014 | Qureshi et al. |
| 8,954,588 B1 | 2/2015 | Bertz et al. |
| 8,984,592 B1 | 3/2015 | Paczkowski et al. |
| 8,989,705 B1 | 3/2015 | Katzer et al. |
| 9,015,068 B1 | 4/2015 | Bertz et al. |
| 9,021,585 B1 | 4/2015 | Paczkowski et al. |
| 9,027,102 B2 | 5/2015 | Katzer et al. |
| 9,049,013 B2 | 6/2015 | Paczkowski et al. |
| 9,049,186 B1 | 6/2015 | Paczkowski et al. |
| 9,066,230 B1 | 6/2015 | Paczkowski et al. |
| 9,069,952 B1 | 6/2015 | Paczkowski et al. |
| 9,104,840 B1 | 8/2015 | Paczkowski et al. |
| 9,118,655 B1 | 8/2015 | Paczkowski et al. |
| 9,161,227 B1 | 10/2015 | Bye et al. |
| 9,161,325 B1 | 10/2015 | Urbanek |
| 9,171,243 B1 | 10/2015 | Cordes et al. |
| 9,177,157 B2 | 11/2015 | Binder |
| 9,183,412 B2 | 11/2015 | Bye et al. |
| 9,183,606 B1 | 11/2015 | Paczkowski et al. |
| 9,185,626 B1 | 11/2015 | Kunkel et al. |
| 9,191,388 B1 | 11/2015 | Paczkowski et al. |
| 9,191,522 B1 | 11/2015 | Krieger et al. |
| 9,208,339 B1 | 12/2015 | Paczkowski et al. |
| 9,210,576 B1 | 12/2015 | Cope et al. |
| 9,215,180 B1 | 12/2015 | Bertz et al. |
| 9,226,145 B1 | 12/2015 | Loman et al. |
| 9,230,085 B1 | 1/2016 | Paczkowski et al. |
| 9,253,589 B2 | 2/2016 | McCann et al. |
| 9,268,959 B2 | 2/2016 | Paczkowski et al. |
| 9,282,898 B2 | 3/2016 | McRoberts et al. |
| 9,324,016 B1 | 4/2016 | Cordes et al. |
| 9,374,363 B1 | 6/2016 | Paczkowski et al. |
| 9,384,498 B1 | 7/2016 | Bertz et al. |
| 9,443,088 B1 | 9/2016 | Bye et al. |
| 9,454,723 B1 | 9/2016 | Cordes et al. |
| 9,473,945 B1 | 10/2016 | Marquardt et al. |
| 9,560,519 B1 | 1/2017 | McCracken, Jr. et al. |
| 9,613,208 B1 | 4/2017 | Paczkowski et al. |
| 9,712,999 B1 | 7/2017 | Cordes et al. |
| 9,779,232 B1 | 10/2017 | Paczkowski et al. |
| 9,811,672 B2 | 11/2017 | Bye et al. |
| 9,817,992 B1 | 11/2017 | Paczkowski et al. |
| 9,819,679 B1 | 11/2017 | Benz et al. |
| 9,838,392 B2 | 12/2017 | Sainio et al. |
| 9,838,868 B1 | 12/2017 | Nelson et al. |
| 9,838,869 B1 | 12/2017 | Bye et al. |

(56) References Cited

U.S. PATENT DOCUMENTS

| | | |
|---|---|---|
| 9,906,958 B2 | 2/2018 | Katzer et al. |
| 9,949,304 B1 | 4/2018 | McCracken et al. |
| 2001/0041591 A1 | 11/2001 | Carroll |
| 2002/0002468 A1 | 1/2002 | Spagna et al. |
| 2002/0007456 A1 | 1/2002 | Peinado et al. |
| 2002/0035697 A1 | 3/2002 | McCurdy et al. |
| 2002/0091569 A1 | 7/2002 | Kitaura et al. |
| 2002/0095389 A1 | 7/2002 | Gaines |
| 2002/0156911 A1 | 10/2002 | Croman et al. |
| 2002/0166070 A1 | 11/2002 | Mualem et al. |
| 2002/0174344 A1 | 11/2002 | Ting |
| 2002/0181503 A1 | 12/2002 | Montgomery |
| 2002/0184325 A1 | 12/2002 | Killcommons et al. |
| 2002/0194361 A1 | 12/2002 | Itoh et al. |
| 2002/0194496 A1 | 12/2002 | Griffin et al. |
| 2003/0045273 A1 | 3/2003 | Pyhalammi et al. |
| 2003/0092435 A1 | 5/2003 | Boivin |
| 2003/0093667 A1 | 5/2003 | Dutta et al. |
| 2003/0110046 A1 | 6/2003 | Cofta |
| 2003/0126225 A1 | 7/2003 | Camble et al. |
| 2003/0172163 A1 | 9/2003 | Fujita et al. |
| 2003/0182347 A1 | 9/2003 | Dehlinger |
| 2003/0216143 A1 | 11/2003 | Roese et al. |
| 2003/0229514 A2* | 12/2003 | Brown ............... A61B 5/1171 705/2 |
| 2003/0237002 A1 | 12/2003 | Oishi et al. |
| 2004/0036572 A1 | 2/2004 | Forster |
| 2004/0043788 A1 | 3/2004 | Mittal |
| 2004/0064351 A1 | 4/2004 | Mikurak |
| 2004/0093274 A1 | 5/2004 | Vanska et al. |
| 2004/0137890 A1 | 7/2004 | Kalke |
| 2004/0158840 A1 | 8/2004 | Rothman et al. |
| 2004/0202319 A1 | 10/2004 | Hussain et al. |
| 2004/0202328 A1 | 10/2004 | Hara |
| 2004/0233844 A1 | 11/2004 | Yu et al. |
| 2004/0234049 A1 | 11/2004 | Melideo |
| 2004/0243810 A1 | 12/2004 | Rindborg et al. |
| 2004/0264372 A1 | 12/2004 | Huang |
| 2005/0015601 A1 | 1/2005 | Tabi |
| 2005/0044375 A1 | 2/2005 | Paatero et al. |
| 2005/0045719 A1 | 3/2005 | Yang |
| 2005/0052994 A1 | 3/2005 | Lee |
| 2005/0091505 A1 | 4/2005 | Riley et al. |
| 2005/0107068 A1 | 5/2005 | Smith et al. |
| 2005/0123596 A1 | 6/2005 | Kohane et al. |
| 2005/0125396 A1 | 6/2005 | Liu |
| 2005/0138433 A1 | 6/2005 | Linetsky |
| 2005/0145688 A1 | 7/2005 | Milenkovic et al. |
| 2005/0153741 A1 | 7/2005 | Chen et al. |
| 2005/0164680 A1 | 7/2005 | Gould |
| 2005/0181796 A1 | 8/2005 | Kumar et al. |
| 2005/0200478 A1 | 9/2005 | Koch et al. |
| 2005/0226468 A1 | 10/2005 | Deshpande et al. |
| 2005/0228892 A1 | 10/2005 | Riley et al. |
| 2005/0235166 A1 | 10/2005 | England et al. |
| 2005/0239481 A1 | 10/2005 | Seligmann |
| 2005/0258250 A1 | 11/2005 | Melick et al. |
| 2005/0272445 A1 | 12/2005 | Zellner |
| 2005/0280557 A1 | 12/2005 | Jha et al. |
| 2005/0283660 A1 | 12/2005 | McKeen et al. |
| 2005/0289355 A1 | 12/2005 | Kitariev et al. |
| 2006/0008256 A1 | 1/2006 | Khedouri et al. |
| 2006/0030291 A1 | 2/2006 | Dawson et al. |
| 2006/0036851 A1 | 2/2006 | DeTreville |
| 2006/0040641 A1 | 2/2006 | Dawson et al. |
| 2006/0053283 A1 | 3/2006 | Feinleib et al. |
| 2006/0074544 A1 | 4/2006 | Morariu et al. |
| 2006/0129488 A1 | 6/2006 | Vincent |
| 2006/0156026 A1 | 7/2006 | Utin |
| 2006/0161626 A1 | 7/2006 | Cardina et al. |
| 2006/0164978 A1 | 7/2006 | Werner et al. |
| 2006/0168637 A1 | 7/2006 | Vysotsky et al. |
| 2006/0171537 A1 | 8/2006 | Enright |
| 2006/0190605 A1 | 8/2006 | Franz et al. |
| 2006/0212853 A1 | 9/2006 | Sutardja |
| 2006/0218320 A1 | 9/2006 | Avraham et al. |
| 2006/0224901 A1 | 10/2006 | Lowe |
| 2006/0239131 A1 | 10/2006 | Nathan et al. |
| 2006/0245438 A1 | 11/2006 | Sajassi et al. |
| 2006/0258289 A1 | 11/2006 | Dua |
| 2006/0259790 A1 | 11/2006 | Asokan et al. |
| 2006/0261949 A1 | 11/2006 | Kim et al. |
| 2006/0277307 A1 | 12/2006 | Bemardin et al. |
| 2006/0277433 A1 | 12/2006 | Largman et al. |
| 2007/0006175 A1 | 1/2007 | Durham et al. |
| 2007/0011061 A1 | 1/2007 | East |
| 2007/0038648 A1 | 2/2007 | Chetwood et al. |
| 2007/0061535 A1 | 3/2007 | Xu et al. |
| 2007/0061570 A1 | 3/2007 | Holtzman et al. |
| 2007/0078988 A1 | 4/2007 | Miloushev et al. |
| 2007/0079120 A1 | 4/2007 | Bade et al. |
| 2007/0093246 A1 | 4/2007 | Adamany et al. |
| 2007/0094273 A1 | 4/2007 | Fritsch et al. |
| 2007/0094691 A1 | 4/2007 | Gazdzinski |
| 2007/0104215 A1 | 5/2007 | Wang et al. |
| 2007/0118880 A1 | 5/2007 | Mauro |
| 2007/0143210 A1 | 6/2007 | Yeung et al. |
| 2007/0150730 A1 | 6/2007 | Conti |
| 2007/0156850 A1 | 7/2007 | Corrion |
| 2007/0162759 A1 | 7/2007 | Buskey et al. |
| 2007/0167167 A1 | 7/2007 | Jiang |
| 2007/0177771 A1 | 8/2007 | Tanaka et al. |
| 2007/0180120 A1 | 8/2007 | Bainbridge et al. |
| 2007/0186212 A1 | 8/2007 | Mazzaferri et al. |
| 2007/0188306 A1 | 8/2007 | Tethrake et al. |
| 2007/0192652 A1 | 8/2007 | Kao et al. |
| 2007/0197261 A1 | 8/2007 | Humbel |
| 2007/0214332 A1 | 9/2007 | Sonoda et al. |
| 2007/0226389 A1 | 9/2007 | Poortman |
| 2007/0276969 A1 | 11/2007 | Bressy et al. |
| 2007/0277223 A1 | 11/2007 | Datta et al. |
| 2007/0280245 A1 | 12/2007 | Rosberg |
| 2007/0283449 A1 | 12/2007 | Blum et al. |
| 2008/0005794 A1 | 1/2008 | Inoue et al. |
| 2008/0011825 A1 | 1/2008 | Giordano et al. |
| 2008/0014867 A1 | 1/2008 | Finn |
| 2008/0020745 A1 | 1/2008 | Bae et al. |
| 2008/0022374 A1 | 1/2008 | Brown et al. |
| 2008/0022389 A1 | 1/2008 | Calcev et al. |
| 2008/0034231 A1 | 2/2008 | Ginter et al. |
| 2008/0051142 A1 | 2/2008 | Calvet et al. |
| 2008/0068166 A1 | 3/2008 | Lauper et al. |
| 2008/0089517 A1 | 4/2008 | Bianco et al. |
| 2008/0092213 A1 | 4/2008 | Wei et al. |
| 2008/0097793 A1 | 4/2008 | Dicks et al. |
| 2008/0100419 A1 | 5/2008 | Jatschka et al. |
| 2008/0108321 A1 | 5/2008 | Taaghol et al. |
| 2008/0109662 A1 | 5/2008 | Natarajan et al. |
| 2008/0121687 A1 | 5/2008 | Buhot |
| 2008/0146280 A1 | 6/2008 | Sasse et al. |
| 2008/0155271 A1 | 6/2008 | Barck et al. |
| 2008/0159129 A1 | 7/2008 | Songhurst et al. |
| 2008/0159131 A1 | 7/2008 | Hoeflin et al. |
| 2008/0160997 A1 | 7/2008 | Kim |
| 2008/0162361 A1 | 7/2008 | Sklovsky et al. |
| 2008/0162637 A1 | 7/2008 | Adamczyk et al. |
| 2008/0168515 A1 | 7/2008 | Benson et al. |
| 2008/0176538 A1 | 7/2008 | Terrill et al. |
| 2008/0188178 A1 | 8/2008 | Maugars et al. |
| 2008/0201212 A1 | 8/2008 | Hammad et al. |
| 2008/0201578 A1 | 8/2008 | Drake |
| 2008/0208681 A1 | 8/2008 | Hammad et al. |
| 2008/0212503 A1 | 9/2008 | Lipford et al. |
| 2008/0232259 A1 | 9/2008 | Thomson |
| 2008/0244758 A1 | 10/2008 | Sahita et al. |
| 2008/0271163 A1 | 10/2008 | Stillerman et al. |
| 2008/0274716 A1 | 11/2008 | Fok et al. |
| 2008/0281953 A1 | 11/2008 | Blaisdell |
| 2008/0304640 A1 | 12/2008 | Reilly |
| 2008/0320577 A1 | 12/2008 | Larduinat |
| 2009/0047923 A1 | 2/2009 | Jain et al. |
| 2009/0049220 A1 | 2/2009 | Conti et al. |
| 2009/0055278 A1 | 2/2009 | Nemani |
| 2009/0070272 A1 | 3/2009 | Jain |

(56) References Cited

U.S. PATENT DOCUMENTS

| | | |
|---|---|---|
| 2009/0075592 A1 | 3/2009 | Nystrom et al. |
| 2009/0089449 A1 | 4/2009 | Day |
| 2009/0113425 A1 | 4/2009 | Ports et al. |
| 2009/0118839 A1 | 5/2009 | Accapadi et al. |
| 2009/0132381 A1 | 5/2009 | Gangi |
| 2009/0144161 A1 | 6/2009 | Fisher |
| 2009/0147958 A1 | 6/2009 | Calcaterra et al. |
| 2009/0154348 A1 | 6/2009 | Newman |
| 2009/0164800 A1 | 6/2009 | Johansson et al. |
| 2009/0182605 A1 | 7/2009 | Lappas et al. |
| 2009/0182634 A1 | 7/2009 | Park et al. |
| 2009/0192915 A1 | 7/2009 | Fernandez |
| 2009/0193491 A1 | 7/2009 | Rao |
| 2009/0204959 A1 | 8/2009 | Anand et al. |
| 2009/0215385 A1 | 8/2009 | Waters et al. |
| 2009/0224919 A1 | 9/2009 | Angell et al. |
| 2009/0227290 A1 | 9/2009 | Chien |
| 2009/0248445 A1* | 10/2009 | Harnick ............ G06Q 30/0251 705/3 |
| 2009/0271321 A1 | 10/2009 | Stafford |
| 2009/0275364 A1 | 11/2009 | Morel et al. |
| 2009/0281947 A1 | 11/2009 | Erel |
| 2009/0289764 A1 | 11/2009 | Chiu |
| 2009/0300599 A1 | 12/2009 | Piotrowski |
| 2009/0312011 A1 | 12/2009 | Huomo et al. |
| 2009/0320028 A1 | 12/2009 | Gellerich et al. |
| 2009/0320048 A1 | 12/2009 | Watt et al. |
| 2010/0031325 A1 | 2/2010 | Maigne et al. |
| 2010/0052844 A1 | 3/2010 | Wesby |
| 2010/0064341 A1 | 3/2010 | Aldera |
| 2010/0066486 A1 | 3/2010 | Park et al. |
| 2010/0075669 A1 | 3/2010 | Sparks et al. |
| 2010/0077487 A1 | 3/2010 | Travis et al. |
| 2010/0082977 A1 | 4/2010 | Boyle et al. |
| 2010/0121156 A1 | 5/2010 | Yoo |
| 2010/0125512 A1 | 5/2010 | Jones et al. |
| 2010/0125904 A1 | 5/2010 | Nice et al. |
| 2010/0127868 A1 | 5/2010 | Hamilton et al. |
| 2010/0128598 A1 | 5/2010 | Gandhewar et al. |
| 2010/0130170 A1 | 5/2010 | Liu et al. |
| 2010/0142517 A1 | 6/2010 | Montemurro et al. |
| 2010/0146589 A1 | 6/2010 | Safa |
| 2010/0153513 A1 | 6/2010 | Zahran |
| 2010/0153721 A1 | 6/2010 | Mellqvist |
| 2010/0162028 A1 | 6/2010 | Frank et al. |
| 2010/0167755 A1 | 7/2010 | Kim et al. |
| 2010/0190469 A1 | 7/2010 | Vanderveen et al. |
| 2010/0191613 A1 | 7/2010 | Raleigh |
| 2010/0198943 A1 | 8/2010 | Harrang et al. |
| 2010/0217709 A1 | 8/2010 | Aabye et al. |
| 2010/0223348 A1 | 9/2010 | Przybysz et al. |
| 2010/0228937 A1 | 9/2010 | Bae et al. |
| 2010/0241847 A1 | 9/2010 | van der Horst et al. |
| 2010/0246818 A1 | 9/2010 | Yao |
| 2010/0263029 A1 | 10/2010 | Tohmo et al. |
| 2010/0269156 A1 | 10/2010 | Hohlfeld et al. |
| 2010/0274726 A1 | 10/2010 | Florek et al. |
| 2010/0279653 A1 | 11/2010 | Poltorak |
| 2010/0281139 A1 | 11/2010 | Deprun |
| 2010/0291896 A1 | 11/2010 | Corda |
| 2010/0299313 A1 | 11/2010 | Orsini et al. |
| 2010/0306353 A1 | 12/2010 | Briscoe et al. |
| 2010/0318802 A1 | 12/2010 | Balakrishnan |
| 2010/0328064 A1 | 12/2010 | Rogel |
| 2011/0010720 A1 | 1/2011 | Smith et al. |
| 2011/0014948 A1 | 1/2011 | Yeh |
| 2011/0021175 A1 | 1/2011 | Florek et al. |
| 2011/0030030 A1 | 2/2011 | Terpening et al. |
| 2011/0035604 A1 | 2/2011 | Habraken |
| 2011/0050713 A1 | 3/2011 | McCrary et al. |
| 2011/0055084 A1 | 3/2011 | Singh |
| 2011/0063093 A1 | 3/2011 | Fung et al. |
| 2011/0072492 A1 | 3/2011 | Mohler et al. |
| 2011/0078081 A1 | 3/2011 | Pirzadeh et al. |
| 2011/0078760 A1 | 3/2011 | De Perthuis |
| 2011/0082711 A1 | 4/2011 | Poeze et al. |
| 2011/0107426 A1 | 5/2011 | Yen et al. |
| 2011/0112968 A1 | 5/2011 | Florek et al. |
| 2011/0113479 A1 | 5/2011 | Ganem |
| 2011/0130635 A1* | 6/2011 | Ross .................. A61B 5/1171 600/301 |
| 2011/0138064 A1 | 6/2011 | Rieger et al. |
| 2011/0145923 A1 | 6/2011 | Largman et al. |
| 2011/0145926 A1 | 6/2011 | Dalcher et al. |
| 2011/0151836 A1 | 6/2011 | Dadu et al. |
| 2011/0154032 A1 | 6/2011 | Mauro |
| 2011/0166883 A1 | 7/2011 | Palmer et al. |
| 2011/0173090 A1 | 7/2011 | Miller et al. |
| 2011/0202916 A1 | 8/2011 | VoBa et al. |
| 2011/0208797 A1 | 8/2011 | Kim |
| 2011/0212707 A1 | 9/2011 | Mahalal |
| 2011/0216701 A1 | 9/2011 | Patel et al. |
| 2011/0218849 A1 | 9/2011 | Rutigliano et al. |
| 2011/0225293 A1 | 9/2011 | Rathod |
| 2011/0226853 A1 | 9/2011 | Soh et al. |
| 2011/0237190 A1 | 9/2011 | Jolivet |
| 2011/0238573 A1 | 9/2011 | Varadarajan |
| 2011/0238992 A1 | 9/2011 | Jancula et al. |
| 2011/0246609 A1 | 10/2011 | Kim |
| 2011/0251892 A1 | 10/2011 | Laracey |
| 2011/0254687 A1 | 10/2011 | Arponen et al. |
| 2011/0258443 A1 | 10/2011 | Barry |
| 2011/0258462 A1 | 10/2011 | Robertson et al. |
| 2011/0269456 A1 | 11/2011 | Krishnaswamy et al. |
| 2011/0276677 A1 | 11/2011 | Osuga et al. |
| 2011/0281558 A1 | 11/2011 | Winter |
| 2011/0294418 A1 | 12/2011 | Chen |
| 2012/0003983 A1 | 1/2012 | Sherlock et al. |
| 2012/0011572 A1 | 1/2012 | Chew et al. |
| 2012/0021683 A1 | 1/2012 | Ma et al. |
| 2012/0023583 A1 | 1/2012 | Sallam |
| 2012/0028575 A1 | 2/2012 | Chen et al. |
| 2012/0029997 A1 | 2/2012 | Khan et al. |
| 2012/0036347 A1 | 2/2012 | Swanson et al. |
| 2012/0040662 A1 | 2/2012 | Rahman et al. |
| 2012/0052801 A1 | 3/2012 | Kulkarni |
| 2012/0072481 A1 | 3/2012 | Nandlall et al. |
| 2012/0072979 A1 | 3/2012 | Cha et al. |
| 2012/0079100 A1 | 3/2012 | McIntyre et al. |
| 2012/0083242 A1 | 4/2012 | Spitz et al. |
| 2012/0084211 A1 | 4/2012 | Petrov et al. |
| 2012/0084438 A1 | 4/2012 | Raleigh et al. |
| 2012/0084836 A1 | 4/2012 | Mahaffey et al. |
| 2012/0089700 A1 | 4/2012 | Safruti et al. |
| 2012/0102202 A1 | 4/2012 | Omar |
| 2012/0108295 A1 | 5/2012 | Schell et al. |
| 2012/0115433 A1 | 5/2012 | Young et al. |
| 2012/0123868 A1 | 5/2012 | Brudnicki et al. |
| 2012/0130839 A1 | 5/2012 | Koh et al. |
| 2012/0131178 A1 | 5/2012 | Zhu et al. |
| 2012/0137101 A1 | 5/2012 | Arcese et al. |
| 2012/0137117 A1 | 5/2012 | Bosch et al. |
| 2012/0137119 A1 | 5/2012 | Doerr et al. |
| 2012/0143703 A1 | 6/2012 | Wall et al. |
| 2012/0147750 A1 | 6/2012 | Pelletier et al. |
| 2012/0149327 A1 | 6/2012 | Raboisson et al. |
| 2012/0149338 A1 | 6/2012 | Roundtree |
| 2012/0150601 A1 | 6/2012 | Fisher |
| 2012/0154413 A1 | 6/2012 | Kim et al. |
| 2012/0158467 A1 | 6/2012 | Hamad et al. |
| 2012/0159163 A1 | 6/2012 | von Behren et al. |
| 2012/0159612 A1 | 6/2012 | Reisgies |
| 2012/0163206 A1 | 6/2012 | Leung et al. |
| 2012/0166806 A1 | 6/2012 | Zhang et al. |
| 2012/0168494 A1 | 7/2012 | Kim |
| 2012/0178365 A1 | 7/2012 | Katz et al. |
| 2012/0178366 A1 | 7/2012 | Levy et al. |
| 2012/0190332 A1 | 7/2012 | Charles |
| 2012/0191536 A1 | 7/2012 | Chen et al. |
| 2012/0196529 A1 | 8/2012 | Huomo et al. |
| 2012/0196586 A1 | 8/2012 | Grigg et al. |
| 2012/0198519 A1 | 8/2012 | Parla et al. |
| 2012/0202423 A1 | 8/2012 | Tiedemann et al. |
| 2012/0207165 A1 | 8/2012 | Davis |

(56) References Cited

U.S. PATENT DOCUMENTS

| | | |
|---|---|---|
| 2012/0218084 A1 | 8/2012 | Arponen et al. |
| 2012/0220269 A1 | 8/2012 | Feng |
| 2012/0226582 A1 | 9/2012 | Hammad |
| 2012/0226772 A1 | 9/2012 | Grube et al. |
| 2012/0238206 A1 | 9/2012 | Singh et al. |
| 2012/0252480 A1 | 10/2012 | Krutt et al. |
| 2012/0255016 A1 | 10/2012 | Sallam |
| 2012/0258690 A1 | 10/2012 | Chen et al. |
| 2012/0259722 A1 | 10/2012 | Mikurak |
| 2012/0266076 A1 | 10/2012 | Lockhart et al. |
| 2012/0266220 A1 | 10/2012 | Brudnicki et al. |
| 2012/0272306 A1 | 10/2012 | Benaloh et al. |
| 2012/0274444 A1 | 11/2012 | Micali et al. |
| 2012/0282924 A1 | 11/2012 | Tagg et al. |
| 2012/0284195 A1 | 11/2012 | McMillen et al. |
| 2012/0291095 A1 | 11/2012 | Narendra et al. |
| 2012/0295588 A1 | 11/2012 | Chen et al. |
| 2012/0297187 A1 | 11/2012 | Paya et al. |
| 2012/0297202 A1 | 11/2012 | Gallet et al. |
| 2012/0303961 A1 | 11/2012 | Kean et al. |
| 2012/0304286 A1 | 11/2012 | Croll et al. |
| 2012/0309345 A1 | 12/2012 | Wake et al. |
| 2012/0324293 A1 | 12/2012 | Grube et al. |
| 2012/0329425 A1 | 12/2012 | Velusamy et al. |
| 2013/0003543 A1 | 1/2013 | Ludwig |
| 2013/0010641 A1 | 1/2013 | Dinan |
| 2013/0014259 A1 | 1/2013 | Gribble et al. |
| 2013/0019323 A1 | 1/2013 | Arvidsson et al. |
| 2013/0031374 A1 | 1/2013 | Thom et al. |
| 2013/0034081 A1 | 2/2013 | Ban et al. |
| 2013/0035056 A1 | 2/2013 | Prasad et al. |
| 2013/0047197 A1 | 2/2013 | Saroiu et al. |
| 2013/0054474 A1 | 2/2013 | Yeager |
| 2013/0061055 A1 | 3/2013 | Schibuk |
| 2013/0062417 A1 | 3/2013 | Lee et al. |
| 2013/0067552 A1 | 3/2013 | Hawkes et al. |
| 2013/0074067 A1 | 3/2013 | Chowdhry |
| 2013/0086385 A1 | 4/2013 | Poeluev |
| 2013/0086684 A1 | 4/2013 | Mohler |
| 2013/0086695 A1 | 4/2013 | Lakshminarayanan |
| 2013/0097302 A9 | 4/2013 | Khedouri et al. |
| 2013/0097657 A1 | 4/2013 | Cardamore et al. |
| 2013/0105565 A1 | 5/2013 | Kamprath |
| 2013/0109307 A1 | 5/2013 | Reisgies et al. |
| 2013/0111095 A1 | 5/2013 | Mehrotra et al. |
| 2013/0117186 A1 | 5/2013 | Weinstein et al. |
| 2013/0124583 A1 | 5/2013 | Ferguson et al. |
| 2013/0125114 A1 | 5/2013 | Frascadore |
| 2013/0136126 A1 | 5/2013 | Wang et al. |
| 2013/0138521 A1 | 5/2013 | Want et al. |
| 2013/0138959 A1 | 5/2013 | Pelly et al. |
| 2013/0140360 A1 | 6/2013 | Graylin |
| 2013/0143489 A1 | 6/2013 | Morris et al. |
| 2013/0145429 A1 | 6/2013 | Mendel et al. |
| 2013/0159021 A1 | 6/2013 | Felsher |
| 2013/0159186 A1 | 6/2013 | Brudnicki et al. |
| 2013/0159710 A1 | 6/2013 | Khan |
| 2013/0160120 A1 | 6/2013 | Malaviya et al. |
| 2013/0174147 A1 | 7/2013 | Sahita et al. |
| 2013/0175984 A1 | 7/2013 | Yamazaki et al. |
| 2013/0191632 A1 | 7/2013 | Spector et al. |
| 2013/0212704 A1 | 8/2013 | Shablygin et al. |
| 2013/0231098 A1 | 9/2013 | Jonas et al. |
| 2013/0260791 A1 | 10/2013 | Malinovskiy et al. |
| 2013/0262264 A1 | 10/2013 | Karstoft |
| 2013/0263212 A1 | 10/2013 | Faltyn et al. |
| 2013/0290359 A1 | 10/2013 | Eronen et al. |
| 2013/0290709 A1 | 10/2013 | Muppidi et al. |
| 2013/0310003 A1 | 11/2013 | Sadhvani et al. |
| 2013/0313314 A1 | 11/2013 | Jeng et al. |
| 2013/0331067 A1 | 12/2013 | Coussemaeker et al. |
| 2013/0332456 A1 | 12/2013 | Arkin |
| 2013/0343181 A1 | 12/2013 | Stroud et al. |
| 2013/0347064 A1 | 12/2013 | Aissi |
| 2013/0347103 A1 | 12/2013 | Veteikis et al. |
| 2014/0007182 A1 | 1/2014 | Qureshi et al. |
| 2014/0007222 A1 | 1/2014 | Qureshi et al. |
| 2014/0052562 A1 | 2/2014 | Oliveira et al. |
| 2014/0059642 A1 | 2/2014 | Deasy et al. |
| 2014/0074508 A1 | 3/2014 | Ying et al. |
| 2014/0089243 A1 | 3/2014 | Oppenheimer |
| 2014/0089699 A1 | 3/2014 | O'Connor et al. |
| 2014/0104287 A1 | 4/2014 | Nalluri et al. |
| 2014/0106709 A1 | 4/2014 | Palamara et al. |
| 2014/0141718 A1 | 5/2014 | Stromberg et al. |
| 2014/0143826 A1 | 5/2014 | Sharp et al. |
| 2014/0155025 A1 | 6/2014 | Parker et al. |
| 2014/0166745 A1 | 6/2014 | Graef et al. |
| 2014/0173747 A1 | 6/2014 | Govindaraju |
| 2014/0188412 A1 | 7/2014 | Mahajan et al. |
| 2014/0188738 A1 | 7/2014 | Huxham |
| 2014/0200051 A1 | 7/2014 | Liu |
| 2014/0215196 A1 | 7/2014 | Berlin |
| 2014/0222955 A1 | 8/2014 | Islam et al. |
| 2014/0245444 A1 | 8/2014 | Lutas et al. |
| 2014/0254381 A1 | 9/2014 | Racz et al. |
| 2014/0267332 A1 | 9/2014 | Chhabra et al. |
| 2014/0279523 A1 | 9/2014 | Lynam et al. |
| 2014/0279556 A1 | 9/2014 | Priebatsch et al. |
| 2014/0279558 A1 | 9/2014 | Kadi et al. |
| 2014/0298026 A1 | 10/2014 | Isozaki et al. |
| 2014/0331279 A1 | 11/2014 | Aissi et al. |
| 2015/0032976 A1 | 1/2015 | Chapier et al. |
| 2015/0106805 A1 | 4/2015 | Melander et al. |
| 2015/0172928 A1 | 6/2015 | Katzer et al. |
| 2015/0358455 A1 | 12/2015 | Mosher et al. |
| 2016/0004876 A1 | 1/2016 | Bye et al. |
| 2016/0150478 A1 | 5/2016 | Li et al. |
| 2016/0323731 A1 | 11/2016 | Mohammed et al. |
| 2017/0026840 A1 | 1/2017 | Eyal |

FOREIGN PATENT DOCUMENTS

| | | |
|---|---|---|
| JP | 6171245 B2 | 8/2017 |
| JP | 6332766 B2 | 5/2018 |
| WO | 2011025433 A1 | 3/2011 |
| WO | 2012064171 A1 | 5/2012 |
| WO | WO2012085593 A1 | 6/2012 |
| WO | 2013170228 A2 | 11/2013 |
| WO | 2014004590 A1 | 1/2014 |
| WO | 2014018575 A2 | 1/2014 |
| WO | 2014025687 A2 | 2/2014 |
| WO | 2014158431 A1 | 10/2014 |

OTHER PUBLICATIONS

Notice of Allowance dated Nov. 18, 2016, U.S. Appl. No. 13/802,404, filed Mar. 13, 2013.

FAIPP Pre-Interview Communication dated Oct. 5, 2016, U.S. Appl. No. 15/069,921, filed Mar. 14, 2016.

McCracken, Billy Gene, Jr., et al. "Mobile Communication Device Profound Identity Brokering Framework", filed Nov. 30, 2016, U.S. Appl. No. 15/365,934.

Final Office Action dated Jun. 28, 2018, U.S. Appl. No. 14/939,887, filed Nov. 12, 2015.

Office Action dated Jun. 11, 2018, U.S. Appl. No. 15/719,813, filed Sep. 29, 2017.

FAIPP Pre-Interview Communication dated Aug. 5, 2015, U.S. Appl. No. 13/857,141, filed Apr. 4, 2013.

Notice of Allowance dated Dec. 17, 2015, U.S. Appl. No. 13/857,141, filed Apr. 4, 2013.

Restriction Requirement dated Jan. 5, 2015, U.S. Appl. No. 13/857,139, filed Apr. 4, 2013.

FAIPP Pre-Interview Communication dated Jun. 2, 2015, U.S. Appl. No. 13/857,139, filed Apr. 4, 2013.

Office Action dated Nov. 19, 2015, U.S. Appl. No. 13/857,139, filed Apr. 4, 2013.

FAIPP Pre-Interview Communication dated Mar. 2, 2015, U.S. Appl. No. 13/857,138, filed Apr. 4, 2013.

First Action Interview Office Action dated Apr. 20, 2015, U.S. Appl. No. 13/857,138, filed Apr. 4, 2013.

(56) References Cited

OTHER PUBLICATIONS

Notice of Allowance dated Jun. 11, 2015, U.S. Appl. No. 13/857,138, filed Apr. 4, 2013.
FAIPP Pre-Interview Communication dated Dec. 27, 2011, U.S. Appl. No. 12/486,873, filed Jun. 18, 2009.
First Action Interview Office Action dated Feb. 13, 2012, U.S. Appl. No. 12/486,873, filed Jun. 18, 2009.
Office Action dated Jul. 5, 2012, U.S. Appl. No. 12/486,873, filed Jun. 18, 2009.
Final Office Action dated Feb. 1, 2013, U.S. Appl. No. 12/486,873, filed Jun. 18, 2009.
Notice of Allowance dated Jan. 28, 2014, U.S. Appl. No. 12/486,873, filed Jun. 18, 2009.
Zimmerman, Ann, "Check Out the Future of Shopping", The Wall Street Journal, Business, May 18, 2011, http://online.wsj,com/article/SB10001424052748703421204576329253050634700.html.
Garry, Michael, Kroger Test Prepares for Mobile Future:, SN, Supermarket News, Jun. 13, 2011, http://supermarketnews.com/technology/kroger-test-prepares-mobile-future.
Jones, Sally, "Industry Trends in POS Hardware for Mobile Devices", Aug. 31, 2011, http://pointofsale.com/20110831734/Mobile-POS-News/industry-trends-in-pos-hardware-for-mobile-devices.html.
Foreign Communication from a Related Counterpart—International Search Report and Written Opinion, dated Dec. 2, 2013, PCT/US13/40673, filed on May 10, 2013.
Foreign Communication from a Related Counterpart—International Preliminary Report on Patentability, dated Nov. 20, 2014, PCT/US13/40673, filed on May 10, 2013.
Giesecke & Devrient, "The OTA Platform in the World of LTE", Jan. 2011, http://www.gi-de.com/gd_media/media/en/documents/brochures/mobile_security_2/cste_1/OTA-and-LTE.pdf.
Pesonen, Lauri, "Development of Mobile Payment Ecosystem—NFC Based Payment Services", Aug. 27, 2008.
Foreign Communication from a Related Counterpart—International Search Report and Written Opinion, dated Feb. 1, 2014, PCT/US13/47729, filed on Jun. 25, 2013.
Foreign Communication from a Related Counterpart—International Preliminary Report on Patentability, dated Jan. 8, 2015, PCT/US13/47729, filed on Jun. 25, 2013.
Foreign Communication from a Related Counterpart—International Search Report and Written Opinion, dated Apr. 22, 2014, PCT/US13/53617, filed on Aug. 5, 2013.
Foreign Communication from a Related Counterpart—International Preliminary Report on Patentability, dated Feb. 19, 2015, PCT/US13/53617, filed on Aug. 5, 2013.
Foreign Communication from a Related Counterpart—International Search Report and Written Opinion, dated Feb. 4, 2014, PCT/US13/51750, filed on Jul. 24, 2013.
Foreign Communication from a Related Counterpart—International Preliminary Report on Patentability, dated Feb. 5, 2015, PCT/US13/51750, filed on Jul. 24, 2013.
Foreign Communication from a Related Counterpart—International Search Report and Written Opinion, dated Jul. 11, 2014, PCT/US14/16651, filed on Feb. 16, 2014.
Foreign Communication from a Related Counterpart—International Preliminary Report on Patentability, dated Sep. 24, 2015, PCT/US14/16651, filed on Feb. 16, 2014.
Ahmed, Farid, et al., "Correlation-based Watermarking Method for Imagine Authentication Applications", Society of Photo-Optical Instrumentation Engineers, Feb. 17, 2004, pp. 1834-1838.
Perrig, Adrian, et al., "SPINS: Security Protocols for Sensor Networks," ACM, Sep. 2002, vol. 8, pp. 521-534.
Clark, CJ., et al. "Anti-tamper JTAG TAP design enables DRM to JTAG registers and P1687 on-chip instruments", 2010 IEEE, International Symposium on Hardware-Oriented Security and Trust (HOST). Pub. Date: 2010. Relevant pp. 19-24. http://ieeexplore.ieee.org/stamp/stamp.jsp?tp=&arnumber=5513119.
Lee, Jeremy, et al., "A Low-Cost Solution for Protecting IPs Against Scan-Based Side Channel Attacks," 24th IEEE VLSI Test Symposium. Pub. Date: 2006. http//ieeexplore.ieee.org/stamp/stamp.jsp?tp=&arnumber=1617569.
Henderson, Tristan, et al., "On the Wire, Congestion Pricing: Paying Your Way in Communications Networks," University College London, Sep./Oct. 2001, retrieved from: http://tristan.host.cs.st-andrews.ac.uk!research/pubs/ieeeic01.pdf.
Dietrich, Kurt, et al., "Implementation Aspects of Mobile and Embedded Trusted Computing," Institute for Applied Information Processing and Communications, Trusted Computing Interaction Conference, 2009.
Bye, Stephen James, et al., "Protection for Multimedia Files Pre-Downloaded to a Mobile Device," filed Apr. 15, 2013, U.S. Appl. No. 13/863,376.
Bertz, Lyle T., et al., "Framework for Real-Time Brokering of Digital Content Delivery," filed Mar. 17, 2015, U.S. Appl. No. 14/659,614.
Paczkowski, Lyle W., et al., "Trusted Security Zone Enhanced with Trusted Hardware Drivers," filed Mar. 13, 2013, U.S. Appl. No. 13/802,404.
Paczkowski, Lyle W., et al., "Restricting Access of a Portable Communication Device to Confidential Data or Applications via a Remote Network Based on Event Triggers Generated by the Portable Communication Device," filed Mar. 15, 2013, U.S. Appl. No. 13/844,282.
Bye, Stephen James, et al., "Delivering Digital Content to a Mobile Device via a Digital Rights Clearing House", filed Apr. 10, 2013, U.S. Appl. No. 13/860,338.
McCracken, Billy Gene, Jr., et al. "Mobile Communication Device Profound Identity Brokering Framework", filed Jun. 6, 2013, U.S. Appl. No. 13/912,190.
Neson, Tracy L., et al., "Mated Universal Serial Bus (USB) Wireless Dongles Configured with Destination Addresses," filed Jan. 26, 2015, U.S. Appl. No. 14/606,011.
Paczkowski, Lyle W., et al., "Trusted Code Generation and Verification to Prevent Fraud from Maleficent External Devices that Capture Data," filed Jan. 14, 2015, U.S. Appl. No. 14/596,218.
Marquardt, et al., "Infrastructure for Secure Short Message Transmission," filed Apr. 7, 2015, U.S. Appl. No. 14/681,077.
Cordes, Kevin R., et al., "Digest of Biographical Information for an Electronic Device with Static and Dynamic Portions," filed on Apr. 4, 2013, U.S. Appl. No. 13/857,141.
Cordes, Kevin R., et al., "Digest of Biographical Information for an Electronic Device with Static and Dynamic Portions," filed on Mar. 14, 2016, U.S. Appl. No. 15/069,921.
Cordes, Kevin R., et al., "Radio Frequency Identity (RFID) Chip Electrically and Communicatively Coupled to Motherboard of Mobile Communication Device," filed on Apr. 4, 2013, U.S. Appl. No. 13/857,139.
FAIPP Pre-Interview Communication dated Mar. 21, 2017, U.S. Appl. No. 14/855,364, filed Sep. 15, 2015.
European Examination Report dated Feb. 14, 2017, EPC Application Serial No. 14775613.4, filed on Jul. 8, 2015.
Final Office Action dated Mar. 9, 2017, U.S. Appl. No. 13/860,338, filed Apr. 10, 2013.
FAIPP Office Action dated Apr. 5, 2017, U.S. Appl. No. 14/596,218, filed Jan. 14, 2015.
Office Action dated Mar. 8, 2017, U.S. Appl. No. 14/947,257, filed Nov. 20, 2015.
Notice of Allowance dated Mar. 10, 2017, U.S. Appl. No. 15/069,921, filed Mar. 14, 2016.
Paczkowski, Lyle W., et al., "System and Method for Secure USIM Wireless Network Access," filed Nov. 20, 2015, U.S. Appl. No. 14/947,257.
Decision on Appeal dated Sep. 15, 2017, U.S. Appl. No. 14/632,850, filed Feb. 26, 2015.
European Examination Report dated Sep. 20, 2017, EPC Application Serial No. 14775613.4, filed on Jul. 8, 2015.
Notice of Allowance dated Jul. 28, 2017, U.S. Appl. No. 13/860,338, filed Apr. 10, 2013.
Notice of Allowance dated Aug. 7, 2017, U.S. Appl. No. 14/606,011, filed Jan. 26, 2015.

(56) References Cited

OTHER PUBLICATIONS

Paczkowski, Lyle W., et al., "System and Method for Secure USIM Wireless Network Access," filed Sep. 29, 2017, U.S. Appl. No. 15/719,813.
Marquardt, Ronald R., et al., "Data Link Layer Trust Signaling in Communication Network," filed Jul. 11, 2017, U.S. Appl. No. 15/646,842.
European Examination Report dated Jun. 1, 2016, EPC Application Serial No. 14775613.4, filed on Jul. 8, 2015.
Office Action dated Aug. 25, 2016, U.S. Appl. No. 13/860,338, filed Apr. 10, 2013.
Notice of Allowance dated Aug. 24, 2016, U.S. Appl. No. 13/912,190, filed Jun. 6, 2013.
FAIPP Pre-Interview Communication dated Aug. 8, 2016, U.S. Appl. No. 14/596,218, filed Jan. 14, 2015.
Notice of Allowance dated Jun. 15, 2016, U.S. Appl. No. 14/681,077, filed Apr. 7, 2015.
Eastlake, 3rd Motorola labs T Hansen AT&T Labs D: "US Secure Hash Algorithms," MPEG Meeting Mar. 16, 2011 to Mar. 23, 2011, Geneva, XP15047395A, ISSN: 0000-0003.
Hamdare, Safa, et al., "Securing SMS Based One Time Password Technique from Man in the Middle Attach," IJETT, vol. 11 Issue 3, May 2014.
Japanese Office Action dated Jan. 16, 2018, Japanese Application Serial No. 2-2016-500275, filed on Jun. 25, 2015.
Japanese Decision for Grant dated Apr. 3, 2018, Japanese Application Serial No. 2-2016-500275, filed on Jun. 25, 2015.
FAIPP Pre-Interview Communication dated Feb. 7, 2018, U.S. Appl. No. 14/939,887, filed Nov. 12, 2015.
Paczkowski, Lyle W., et al., "Secure and Trusted Device-Based Billing and Charging Process Using Privilege for Network Proxy Authentication and Audit," filed Nov. 12, 2015, U.S. Appl. No. 14/939,887.
Notice of Allowance dated Jul. 6, 2015, U.S. Appl. No. 13/844,145, filed Mar. 15, 2013.
FAIPP Pre-Interview Communication dated Mar. 1, 2016, U.S. Appl. No. 13/863,376, filed Apr. 15, 2013.
FAIPP Pre-Interview Communication dated Apr. 3, 2014, U.S. Appl. No. 13/802,383, filed Mar. 13, 2013.
First Action Interview Office Action dated May 23, 2014, U.S. Appl. No. 13/802,383, filed Mar. 13, 2013.
Notice of Allowance dated Jul. 8, 2014, U.S. Appl. No. 13/802,383, filed Mar. 13, 2013.
FAIPP Pre-Interview Communication dated Feb. 12, 2015, U.S. Appl. No. 14/066,661, filed Oct. 29, 2013.
Notice of Allowance dated Jul. 6, 2015, U.S. Appl. No. 14/066,661, filed Oct. 29, 2013.
Restriction Requirement dated Aug. 14, 2014, U.S. Appl. No. 13/594,777, filed Aug. 25, 2012.
Notice of Allowance dated Dec. 3, 2014, U.S. Appl. No. 13/594,777, filed Aug. 25, 2012.
Notice of Allowance dated Nov. 9, 2015, U.S. Appl. No. 14/659,614, filed Mar. 17, 2015.
FAIPP Pre-Interview Communication dated Jul. 17, 2014, U.S. Appl. No. 13/594,778, filed Aug. 25, 2012.
Notice of Allowance dated Sep. 19, 2014, U.S. Appl. No. 13/594,778, filed Aug. 25, 2012.
FAIPP Pre-Interview Communication dated Jul. 17, 2014, U.S. Appl. No. 13/594,779, filed Aug. 25, 2012.
First Action Interview Office Action dated Dec. 3, 2014, U.S. Appl. No. 13/594,779, filed Aug. 25, 2012.
Notice of Allowance dated Aug. 14, 2015, U.S. Appl. No. 13/594,779, filed Aug. 25, 2012.
Office Action dated May 5, 2014, U.S. Appl. No. 13/786,450, filed Mar. 5, 2013.
Final Office Action dated Nov. 7, 2014, U.S. Appl. No. 13/786,450, filed Mar. 5, 2013.
Notice of Allowance dated Feb. 26, 2015, U.S. Appl. No. 13/786,450, filed Mar. 5, 2013.
FAIPP Pre-Interview Communication dated Aug. 6, 2014, U.S. Appl. No. 13/831,486, filed Mar. 14, 2013.
Notice of Allowance dated Sep. 26, 2014, U.S. Appl. No. 13/831,486, filed Mar. 14, 2013.
FAIPP Pre-Interview Communication dated Nov. 7, 2014, U.S. Appl. No. 13/802,404, filed Mar. 13, 2013.
First Action Interview Office Action dated Apr. 7, 2015, U.S. Appl. No. 13/802,404, filed Mar. 13, 2013.
Final Office Action dated Aug. 27, 2015, U.S. Appl. No. 13/802,404, filed Mar. 13, 2013.
Advisory Action dated Nov. 16, 2015, U.S. Appl. No. 13/802,404, filed Mar. 13, 2013.
FAIPP Pre-Interview Communication dated Dec. 16, 2014, U.S. Appl. No. 13/898,435, filed May 20, 2013.
Notice of Allowance dated Feb. 20, 2015, U.S. Appl. No. 13/898,435, filed May 20, 2013.
FAIPP Pre-Interview Communication dated Mar. 26, 2015, U.S. Appl. No. 13/939,175, filed Jul. 10, 2013.
Notice of Allowance dated Jul. 7, 2015, U.S. Appl. No. 13/939,175, filed Jul. 10, 2013.
FAIPP Pre-Interview Communication dated Oct. 29, 2014, U.S. Appl. No. 13/844,282, filed Mar. 15, 2013.
Final Office Action dated Mar. 24, 2015, U.S. Appl. No. 13/844,282, filed Mar. 15, 2013.
Advisory Action dated Jun. 10, 2015, U.S. Appl. No. 13/844,282, filed Mar. 15, 2013.
Office Action dated Aug. 24, 2015, U.S. Appl. No. 13/844,282, filed Mar. 15, 2013.
Notice of Allowance dated Feb. 26, 2016, U.S. Appl. No. 13/844,282, filed Mar. 15, 2013.
FAIPP Pre-Interview Communication dated Oct. 21, 2014, U.S. Appl. No. 13/844,325, filed Mar. 15, 2013.
Notice of Allowance dated Dec. 19, 2014, U.S. Appl. No. 13/844,325, filed Mar. 15, 2013.
Notice of Allowance dated Jan. 2, 2015, U.S. Appl. No. 13/831,463, filed Mar. 14, 2013.
FAIPP Pre-Interview Communication dated Mar. 24, 2015, U.S. Appl. No. 13/964,112, filed Aug. 12, 2013.
Notice of Allowance dated Aug. 3, 2015, U.S. Appl. No. 13/964,112, filed Aug. 12, 2013.
Restriction Requirement dated Jan. 12, 2016, U.S. Appl. No. 13/912,190, filed Jun. 6, 2013.
FAIPP Pre-Interview Communication dated Mar. 11, 2016, U.S. Appl. No. 13/912,190, filed Jun. 6, 2013.
FAIPP Pre-Interview Communication dated Apr. 15, 2015, U.S. Appl. No. 14/085,474, filed Nov. 20, 2013.
Notice of Allowance dated May 29, 2015, U.S. Appl. No. 14/085,474, filed Nov. 20, 2013.
FAIPP Pre-Interview Communication dated Feb. 4, 2015, U.S. Appl. No. 14/075,663, filed Nov. 8, 2013.
First Action Interview Office Action dated Apr. 10, 2015, U.S. Appl. No. 14/075,663, filed Nov. 8, 2013.
Notice of Allowance dated Jul. 1, 2015, U.S. Appl. No. 14/075,663, filed Nov. 8, 2013.
FAIPP Pre-Interview Communication dated Feb. 24, 2015, U.S. Appl. No. 14/163,047, filed Jan. 24, 2014.
Notice of Allowance dated Apr. 9, 2015, U.S. Appl. No. 14/163,047, filed Jan. 24, 2014.
Notice of Allowance dated Jul. 22, 2015, U.S. Appl. No. 14/229,532, filed Mar. 28, 2014.
Notice of Allowance dated Aug. 28, 2015, U.S. Appl. No. 14/446,330, filed Jul. 29, 2014.
FAIPP Pre-Interview Communication dated Nov. 18, 2015, U.S. Appl. No. 14/681,077, filed Apr. 7, 2015.
Notice of Allowance dated Jul. 6, 2017, U.S. Appl. No. 14/855,364, filed Sep. 15, 2015.
Japanese Decision for Grant dated Jun. 6, 2017, JP Application Serial No. 2015-524404.
Advisory Action dated Jun. 1, 2017, U.S. Appl. No. 13/860,338, filed Apr. 10, 2013.
FAIPP Pre-Interview Communication dated Apr. 27, 2017, U.S. Appl. No. 14/606,011, filed Jan. 26, 2015.

(56) References Cited

OTHER PUBLICATIONS

Notice of Allowance dated May 30, 2017, U.S. Appl. No. 14/596,218, filed Jan. 14, 2015.
FAIPP Pre-Interview Communication dated May 9, 2017, U.S. Appl. No. 14/853,492, filed Sep. 14, 2015.
Notice of Allowance dated Jul. 7, 2017, U.S. Appl. No. 14/853,492, filed Sep. 14, 2015.
Notice of Allowance dated Jul. 24, 2017, U.S. Appl. No. 14/947,257, filed Nov. 20, 2015.
Twin Connect—"User Guide for Windows"; 30 pages; dated 2013.
WiseGEEK, "What is a USB Dongle?," http://www.wisegeek.com/what-is-a-usb-dongle.htm, four pages, dated Jul. 25, 2017.
Bertz, Lyle T., et al., "Hardware Assisted Provenance Proof of Named Data Networking Associated to Device Data, Addresses, Services, and Servers," filed Sep. 14, 2015, U.S. Appl. No. 14/853,492.
FAIPP Pre-Interview Communication dated Mar. 20, 2014, U.S. Appl. No. 13/482,731, filed May 29, 2012.
Notice of Allowance dated May 27, 2014, U.S. Appl. No. 13/482,731, filed May 29, 2012.
FAIPP Pre-Interview Communication dated Oct. 24, 2012, U.S. Appl. No. 13/463,797, filed May 3, 2012.
Notice of Allowance dated Mar. 1, 2013, U.S. Appl. No. 13/463,797, filed May 3, 2012.
FAIPP Pre-Interview Communication dated Jun. 12, 2013, U.S. Appl. No. 13/440,980, filed Apr. 5, 2012.
Final Office Action dated Sep. 9, 2013, U.S. Appl. No. 13/440,980, filed Apr. 5, 2012.
Notice of Allowance dated Nov. 29, 2013, U.S. Appl. No. 13/440,980, filed Apr. 5, 2012.
FAIPP Pre-Interview Communication dated Oct. 24, 2012, U.S. Appl. No. 13/463,801, filed May 3, 2012.
Notice of Allowance dated Mar. 14, 2013, U.S. Appl. No. 13/463,801, filed May 3, 2012.
FAIPP Pre-Interview Communication dated Jul. 25, 2013, U.S. Appl. No. 13/470,203, filed May 11, 2012.
Final Office Action dated Mar. 27, 2014, U.S. Appl. No. 13/470,203, filed May 11, 2012.
Advisory Action dated May 29, 2014, U.S. Appl. No. 13/470,203, filed May 11, 2012.
Office Action dated Aug. 29, 2014, U.S. Appl. No. 13/470,203, filed May 11, 2012.
Notice of Allowance dated Dec. 22, 2014, U.S. Appl. No. 13/470,203, filed May 11, 2012.
FAIPP Pre-Interview Communication dated Jul. 2, 2015, U.S. Appl. No. 14/632,850, filed Feb. 26, 2015.
Final Office Action dated Nov. 6, 2015, U.S. Appl. No. 14/632,850, filed Feb. 26, 2015.
Advisory Action dated Jan. 29, 2016, U.S. Appl. No. 14/632,850, filed Feb. 26, 2015.
FAIPP Pre-Interview Communication dated May 12, 2014, U.S. Appl. No. 13/294,177, filed Nov. 11, 2011.
Notice of Allowance dated Oct. 8, 2014, U.S. Appl. No. 13/294,177, filed Nov. 11, 2011.
FAIPP Pre-Interview Communication dated Mar. 25, 2015, U.S. Appl. No. 13/532,588, filed Jun. 25, 2012.
FAIPP Office Action Sep. 15, 2015, U.S. Appl. No. 13/532,588, filed Jun. 25, 2012.
Notice of Allowance dated Nov. 5, 2015, U.S. Appl. No. 13/532,588, filed Jun. 25, 2012.
Supplemental Notice of Allowance dated Nov. 16, 2015, U.S. Appl. No. 13/532,588, filed Jun. 25, 2012.
FAIPP Pre-Interview Communication dated Sep. 25, 2014, U.S. Appl. No. 13/533,969, filed Jun. 27, 2012.
Notice of Allowance dated Feb. 5, 2015, U.S. Appl. No. 13/533,969, filed Jun. 27, 2012.
FAIPP Pre-Interview Communication dated Jun. 6, 2013, U.S. Appl. No. 13/571,348, filed Aug. 10, 2012.
Office Action dated Sep. 25, 2013, U.S. Appl. No. 13/571,348, filed Aug. 10, 2012.
Final Office Action dated Apr. 10, 2014, U.S. Appl. No. 13/571,348, filed Aug. 10, 2012.
Advisory Action dated Jun. 23, 2014, U.S. Appl. No. 13/571,348, filed Aug. 10, 2012.
Office Action dated Dec. 15, 2014, U.S. Appl. No. 13/571,348, filed Aug. 10, 2012.
Notice of Allowance dated Jun. 17, 2015, U.S. Appl. No. 13/571,348, filed Aug. 10, 2012.
Restriction Requirement dated Jan. 2, 2015, U.S. Appl. No. 13/762,319, filed Feb. 7, 2013.
FAIPP Pre-Interview Communication dated Mar. 10, 2015, U.S. Appl. No. 13/762,319, filed Feb. 7, 2013.
Notice of Allowance dated Jun. 9, 2015, U.S. Appl. No. 13/762,319, filed Feb. 7, 2013.
Notice of Allowance dated Aug. 30, 2013, U.S. Appl. No. 13/540,437, filed Jul. 2, 2012.
FAIPP Pre-Interview Communication dated May 21, 2015, U.S. Appl. No. 14/090,667, filed Nov. 26, 2013.
Notice of Allowance dated Aug. 4, 2015, U.S. Appl. No. 14/090,667, filed Nov. 26, 2013.
Restriction Requirement dated Nov. 1, 2013, U.S. Appl. No. 13/557,213, filed Jul. 25, 2012.
Office Action dated Dec. 19, 2013, U.S. Appl. No. 13/557,213, filed Jul. 25, 2012.
Notice of Allowance dated Jun. 4, 2014, U.S. Appl. No. 13/557,213, filed Jul. 25, 2012.
FAIPP Pre-Interview Communication dated Nov. 27, 2013, U.S. Appl. No. 13/610,856, filed Sep. 11, 2012.
Notice of Allowance dated Jan. 31, 2014, U.S. Appl. No. 13/610,856, filed Sep. 11, 2012.
FAIPP Pre-Interview Communication dated Jun. 5, 2013, U.S. Appl. No. 13/556,200, filed Jul. 24, 2012.
First Action Interview Office Action dated Aug. 19, 2013, U.S. Appl. No. 13/556,200, filed Jul. 24, 2012.
Notice of Allowance dated Oct. 16, 2013, U.S. Appl. No. 13/556,200, filed Jul. 24, 2012.
Notice of Allowance dated Sep. 21, 2015, U.S. Appl. No. 14/148,714, filed Jan. 6, 2014.
FAIPP Pre-Interview Communication dated Aug. 4, 2014, U.S. Appl. No. 13/844,357, filed Mar. 15, 2013.
Notice of Allowance dated Oct. 6, 2014, U.S. Appl. No. 13/844,357, filed Mar. 15, 2013.
FAIPP Pre-Interview Communication dated Nov. 12, 2014, U.S. Appl. No. 13/844,145, filed Mar. 15, 2013.
Final Office Action dated Apr. 7, 2015, U.S. Appl. No. 13/844,145, filed Mar. 15, 2013.
European Examination Report dated Mar. 3, 2016, EPC Application Serial No. , filed on.
Notice of Allowance dated May 2, 2016, U.S. Appl. No. 13/863,376, filed Apr. 15, 2013.
Office Action dated May 17, 2016, U.S. Appl. No. 13/802,404, filed Mar. 13, 2013.
First Action Interview Office Action dated Mar. 28, 2016, U.S. Appl. No. 14/681,077, filed Apr. 7, 2015.
Notice of Allowance dated Mar. 26, 2016, U.S. Appl. No. 13/857,139, filed Apr. 4, 2013.
Notice of Allowance dated Oct. 18, 2017, U.S. Appl. No. 14/632,850, filed Feb. 26, 2015.
FAIPP Pre-Interview Communication dated Oct. 12, 2017, U.S. Appl. No. 15/365,934, filed Nov. 30, 2016.
Notice of Allowance dated Dec. 7, 2017, U.S. Appl. No. 15/365,934, filed Nov. 30, 2016.
Advisory Action dated Aug. 15, 2018, U.S. Appl. No. 14/939,887, filed Nov. 12, 2015.
Pre-Appeal Decision dated Oct. 24, 2018, U.S. Appl. No. 14/939,887, filed on Nov. 12, 2015.

* cited by examiner

END-TO-END TRUSTED COMMUNICATIONS INFRASTRUCTURE

CROSS-REFERENCE TO RELATED APPLICATIONS

This application is a continuation of and claims priority under 35 U.S.C. § 120 to U.S. patent application Ser. No. 13/532,588, filed on Jun. 25, 2012, entitled "End-to-End Trusted Communications Infrastructure", by Leo Michael McRoberts, et al., which is incorporated herein by reference in its entirety for all purposes.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Electronic communications may carry a wide variety of content, for example electronic mail, medical records, financial transactions, and other confidential information. The electronic communications may travel for some of the communication end-to-end path over unsecured communication links where the content may be subject to tampering or intrusion. A variety of security measures have been applied to provide increased security and to raise the level of difficulty for nefarious actors attempting to access the confidential information.

SUMMARY

In an embodiment, a method of delivery of medical data via a trusted end-to-end communication link is disclosed. The method comprises obtaining a measurement of a parameter of a human being by a first sensor, obtaining a biometric from the human being by a second sensor, receiving input from the first and second sensors by a secure application executing in a trusted security zone of a processor, whereby access to the input from the first and second sensors by applications executing in a normal partition of the processor is blocked, wherein the input from the first and second sensors comprises the measurement of the parameter and the biometric, and transmitting a message based on the input from the first and second sensors via a trusted end-to-end communication link to a medical data server, wherein an application that receives the message executes in a trusted security zone of the server.

In an embodiment, a method establishing a trusted end-to-end communication link is disclosed. The method comprises executing a communication application in a trusted security zone of a mobile access terminal, sending a message from the mobile access terminal to a trusted communication application executing in a trusted security zone of a trusted enterprise edge node, and sending the message from the trusted enterprise edge node to a trusted cloudlet executing on in a trusted security zone of a cloud based server.

In an embodiment, a method of accessing medical diagnostic information is disclosed. The method comprises obtaining a measurement of a parameter of a human being from a first sensor and a biometric from the human being from a second sensor, transmitting the measurement of the parameter and the biometric from the first and second sensors, and receiving the measurement of the parameter and the biometric from the first and second sensors by a processor executing in a trusted security zone of a mobile access terminal, whereby access to the measurement of the parameter and the biometric from the first and second sensors by applications executing in a normal execution mode is blocked. The method further comprises transmitting a first message based on the measurement of the parameter and the biometric by the mobile access terminal via a trusted end-to-end communication link to a medical data server, wherein the trusted end-to-end communication link comprises a wireless communication link, and receiving the first message by an application that executes in a trusted security zone of the medical data server. The method further comprises transmitting a second message based on the measurement of the parameter and the biometric by the medical data server via a trusted end-to-end communication link to a computer associated with a medical doctor and determining a medical care instruction for the human being based on the second message.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
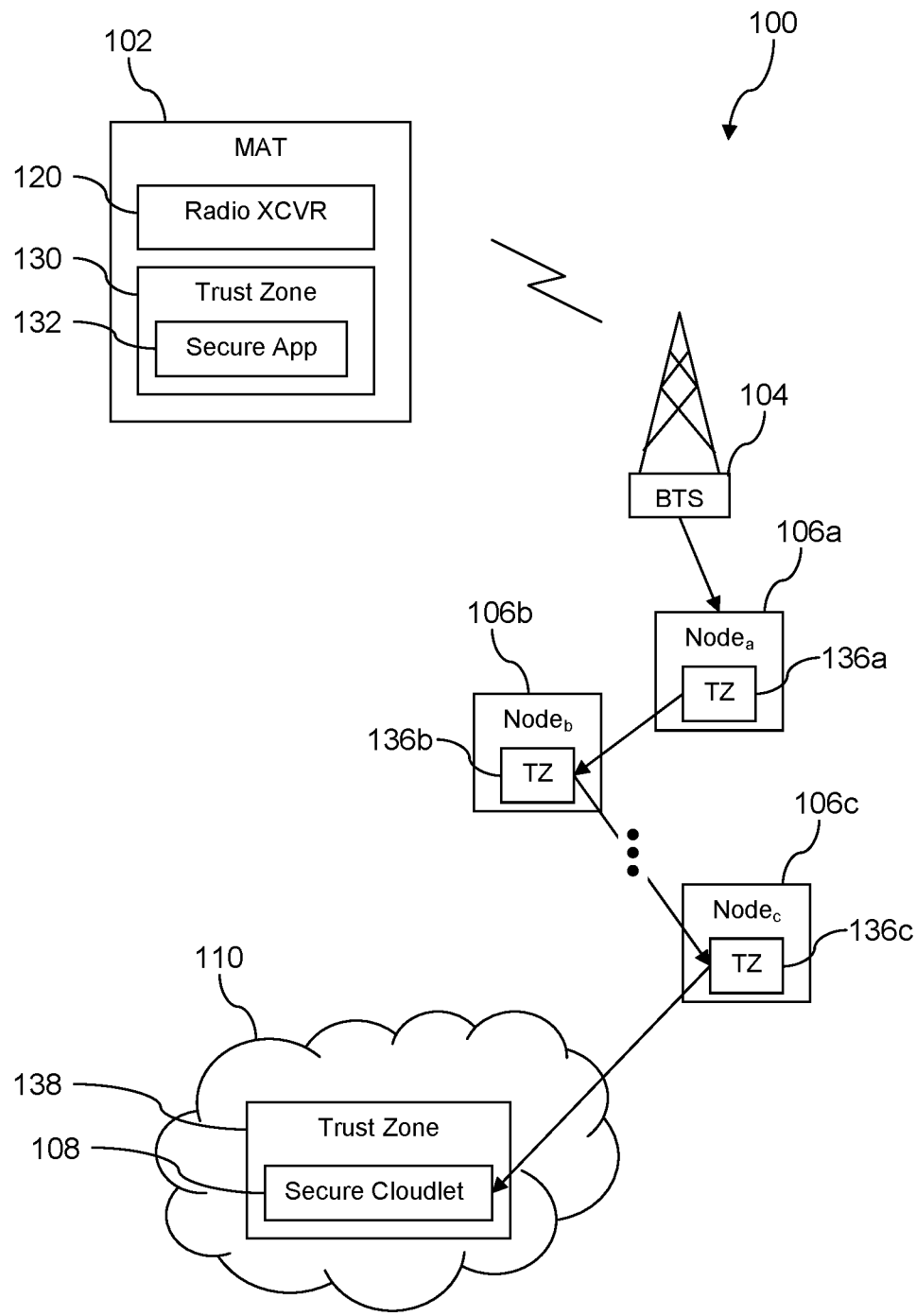
FIG. 1 is an illustration of a communication system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

In an embodiment, a system and methods of providing a trusted end-to-end communication link are described. Trusted communication can be established between two devices each of which are executing their communication processing in a trusted security zone. As described further below, trusted security zones reduce the ability of nefarious applications that may have infiltrated an electronic processing device to read from or write to memory, to read from or write to input/output devices, or to read from or write to communication ports while the subject processor and/or electronic processing device is executing in the trusted security zone. A communication application executing in a trusted security zone can have a high level of confidence that an untrusted application is not executing on the electronic processing device, for example a mobile telephone, at the same time and hence is prevented from interfering with or monitoring the activities of the communication application.

A trusted end-to-end communication link may be established by assuring that all communication applications in the end-to-end communication link that execute at the network layer and/or higher layers execute in trusted security zones of the subject electronic processing devices, for example a mobile phone, a base transceiver station, a media access gateway, Internet routers, switches, server computers, and the like. Prior to a first node transmitting a message over a trusted end-to-end communication link to a second node, the first node may handshake with or otherwise communicate with the second node to pre-arrange for the second node to handle the forthcoming message from the first node in the trusted security zone of the second node. This handshaking may comprise the first node validating the trusted status of the second node. Said in other words, the handshaking may promote the first node evaluating whether the second node is configured to support the trusted end-to-end communication link.

As an electronic message is passed from one network node to the next, each successive node in the trusted end-to-end communication link may validate the continuity of trust by examining and validating trust tokens that are accumulated by the message as it transits the trusted end-to-end communication link. The trust tokens are built and provided by the previous node and/or previous nodes in the trusted end-to-end communication link. The trust tokens comprise indications or information about how the subject message was handled, e.g., processed in a trusted security zone, and may be viewed as a kind of birth certificate or pedigree of the message. Some or all of the trust token may be encrypted to avoid monitoring or tampering by untrusted nodes. Trust tokens may be created by a secure application, such as the communication application that is executing in the trusted security zone to conduct communication over the trusted end-to-end communication link, or by a base layer of functionality and/or utilities provided by the trusted security zone itself.

For example, a secure application executing in the trusted security zone of a mobile phone may send a message to a first trusted network node. The message may comprise content and a first trust token that encrypts information about the mobile phone that establishes that the message was generated by the trusted security zone of the mobile phone. The message may be verified to be trusted by the first trusted network node by examining the first trust token. The first trusted network node may then build a second trust token, extend the message by the addition of the second trust token, and transmit the extended message to a second trusted network node. The message may be verified to be trusted by the second trusted network node by examining the second trust token alone or by examining both the first and the second trust tokens. Through the remainder of the trusted end-to-end communication link, every network node that handles the message at the network layer or higher layer handles the message in a trusted security zone of that node, verifies the continuity of trust by examining one or more trust tokens, builds an additional trust token, extends the message with the additional trust token, and sends the message on to the next trusted network node. At the endpoint of the trusted end-to-end communication link, the message may be consumed by a secure application executing in a trusted security zone of the endpoint device after the continuity of trust of the message is verified. In an alternative embodiment, rather than the message being accompanied by a plurality of trust tokens, the message may be accompanied by a single trust token that may be extended and/or appended to by each successive trusted network node.

In an embodiment, the trusted end-to-end communication link may extend from a mobile access terminal to a base transceiver station (BTS) to an enterprise network via a virtual private network (VPN) connection. The continuity of trust of the connection between the mobile access terminal and the base transceiver station may not be explicitly verified because the air interface of the base transceiver station may be considered to be invulnerable to a hacking attack. The continuity of trust of the virtual private network connection into the enterprise network may not be explicitly verified because it likewise may be considered to be invulnerable to a hacking attack. If the trusted end-to-end communication link then extends out of the enterprise network through a firewall or through a multi-protocol label switching (MPLS) port into the Internet and on to an endpoint device, such as a secure cloudlet executing on a trusted security zone of a server computer operated in a cloud computing service, trust may be provided as described above, with the subject message being handled at the network layer or above layers only by applications executing in trusted security zones on the subject network nodes, each trusted security zone verifying the continuity of trust of the received message and adding an additional trust token or extending the trust token when transmitting the message on to the next node. At the server computer in the cloud, the secure cloudlet executes in a trusted security zone of the server computer and verifies the continuity of trust of the received message and/or the trusted end-to-end communication link.

In an embodiment, a monitor device may comprise a sensor and a biometric scanner or sensor. The sensor may measure or sample a bodily parameter of a human being such as a blood sugar level, a blood thickness, a blood pressure, a bodily temperature, a pulse rate, a heart rhythm, or another parameter. At the same time that the bodily parameter is being sampled, the biometric scanner may capture a biometric signature of the human being whose bodily parameter is being measured. In an embodiment, the monitor device is configured such that taking the sample of the bodily parameter of the human being is inseparably linked to capturing the biometric signature of the same human being. The biometric signature may be used to establish and/or to corroborate the identity of the human being. The biometric signature may be a finger print, a retinal scan, a face scan, a DNA signature, or other. A secure application executing in a trusted security zone of a mobile access terminal or a computer reads the bodily parameter sample and the biometric signature from the monitor device.

The secure application may then package the bodily parameter sample and the biometric signature into a medical record content, build a trusted token, and send a message comprising the medical record content and the trusted token through a trusted end-to-end communication link to a corresponding trusted application executing in a trusted security zone of a medical data server. Alternatively, the trusted token may be built by a base layer of functionality and/or utilities provided by the trusted security zone itself. Sending the message over the trusted end-to-end communication link may assure that the medical record content is maintained in confidence, for example in compliance with FDA and/or HIPAA privacy regulations. In an embodiment, medical records maintained by the medical data server may be accessed over a trusted end-to-end communication link to analyze the medical records for a variety of purposes, for example to conduct treatment efficacy studies and/or to diagnose and determine a treatment regime for a patient, while assuring compliance with FDA and/or HIPAA privacy regulations.

A trusted security zone provides chipsets with a hardware root of trust, a secure execution environment for applications, and secure access to peripherals. A hardware root of trust means the chipset should only execute programs intended by the device manufacturer or vendor and resists software and physical attacks, and therefore remains trusted to provide the intended level of security. The chipset architecture is designed to promote a programmable environment that allows the confidentiality and integrity of assets to be protected from specific attacks. Trusted security zone capabilities are becoming features in both wireless and fixed hardware architecture designs. Providing the trusted security zone in the main mobile device chipset and protecting the hardware root of trust removes the need for separate secure hardware to authenticate the device or user. To ensure the integrity of the applications requiring trusted data, such as a mobile financial services application, the trusted security zone also provides the secure execution environment where only trusted applications can operate, safe from attacks. Security is further promoted by restricting access of non-trusted applications to peripherals, such as data inputs and data outputs, while a trusted application is running in the secure execution environment. In an embodiment, the trusted security zone may be conceptualized as hardware assisted security.

A complete Trusted Execution Environment (TEE) may be implemented through the use of the trusted security zone hardware and software architecture. The Trusted Execution Environment is an execution environment that is parallel to the execution environment of the main mobile device operating system. The Trusted Execution Environment and/or the trusted security zone may provide a base layer of functionality and/or utilities for use of applications that may execute in the trusted security zone. For example, in an embodiment, trust tokens may be generated by the base layer of functionality and/or utilities of the Trusted Execution Environment and/or trusted security zone for use in trusted end-to-end communication links to document a continuity of trust of the communications. Through standardization of application programming interfaces (APIs), the Trusted Execution Environment becomes a place to which scalable deployment of secure services can be targeted. A device which has a chipset that has a Trusted Execution Environment on it may exist in a trusted services environment, where devices in the trusted services environment are trusted and protected against attacks. The Trusted Execution Environment can be implemented on mobile phones and tablets as well as extending to other trusted devices such as personal computers, servers, sensors, medical devices, point-of-sale terminals, industrial automation, handheld terminals, automotive, etc.

The trusted security zone is implemented by partitioning all of the hardware and software resources of the mobile device into two partitions: a secure partition and a normal partition. The secure partition may be implemented by a first physical processor, and the normal partition may be implemented by a second physical processor. Alternatively, the secure partition may be implemented by a first virtual processor, and the normal partition may be implemented by a second virtual processor. Placing sensitive resources in the secure partition can protect against possible attacks on those resources. For example, resources such as trusted software applications may run in the secure partition and have access to hardware peripherals such as a touchscreen or a secure location in memory. Less secure peripherals such as wireless radios may be disabled completely while the secure partition is being accessed, while other peripherals may only be accessed from the secure partition. While the secure partition is being accessed through the Trusted Execution Environment, the main mobile operating system in the normal partition is suspended, and applications in the normal partition are prevented from accessing the secure peripherals and data. This prevents corrupted applications or malware applications from breaking the trust of the device.

The trusted security zone is implemented by partitioning the hardware and software resources to exist in a secure subsystem which is not accessible to components outside the secure subsystem. The trusted security zone is built into the processor architecture at the time of manufacture through hardware logic present in the trusted security zone which enables a perimeter boundary between the secure partition and the normal partition. The trusted security zone may only be manipulated by those with the proper credential and, in an embodiment, may not be added to the chip after it is manufactured. Software architecture to support the secure partition may be provided through a dedicated secure kernel running trusted applications. Trusted applications are independent secure applications which can be accessed by normal applications through an application programming interface in the Trusted Execution Environment on a chipset that utilizes the trusted security zone.

In an embodiment, the normal partition applications run on a first virtual processor, and the secure partition applications run on a second virtual processor. Both virtual processors may run on a single physical processor, executing in a time-sliced fashion, removing the need for a dedicated physical security processor. Time-sliced execution comprises switching contexts between the two virtual processors to share processor resources based on tightly controlled mechanisms such as secure software instructions or hardware exceptions. The context of the currently running virtual processor is saved, the context of the virtual processor being switched to is restored, and processing is restarted in the restored virtual processor. Time-sliced execution protects the trusted security zone by stopping the execution of the normal partition while the secure partition is executing.

The two virtual processors context switch via a processor mode called monitor mode when changing the currently running virtual processor. The mechanisms by which the processor can enter monitor mode from the normal partition are tightly controlled. The entry to monitor mode can be triggered by software executing a dedicated instruction, the Secure Monitor Call (SMC) instruction, or by a subset of the hardware exception mechanisms such as hardware interrupts, which can be configured to cause the processor to switch into monitor mode. The software that executes within monitor mode then saves the context of the running virtual processor and switches to the secure virtual processor.

The trusted security zone runs a separate operating system that is not accessible to the device users. For security purposes, the trusted security zone is not open to users for installing applications, which means users do not have access to install applications in the trusted security zone. This prevents corrupted applications or malware applications from executing powerful instructions reserved to the trusted security zone and thus preserves the trust of the device. The security of the system is achieved at least in part by partitioning the hardware and software resources of the mobile phone so they exist in one of two partitions, the secure partition for the security subsystem and the normal partition for everything else. Placing the trusted security zone in the secure partition and restricting access from the normal partition protects against software and basic hardware attacks. Hardware logic ensures that no secure partition resources can be accessed by the normal partition components or applications. A dedicated secure partition operating system runs in a virtual processor separate from the normal partition operating system that likewise executes in its own virtual processor. Users may install applications on the mobile device which may execute in the normal partition operating system described above. The trusted security zone runs a separate operating system for the secure partition that is installed by the mobile device manufacturer or vendor, and users are not able to install new applications in or alter the contents of the trusted security zone.

Turning now to FIG. 1, a first system 100 for providing trusted end-to-end communication links is described. In an embodiment, the system 100 comprises a mobile access terminal (MAT) 102, a base transceiver station (BTS) 104, a plurality of network nodes 106, and a secure cloudlet 108 executing in a trusted security zone 138 of a server computer located in a cloud computing facility 110. The MAT 102 may be any of a mobile phone, a personal digital assistant (PDA), a media player, a laptop computer, a tablet computer, a notepad computer, or other portable communication device. The network nodes 106 may comprise a first network node 106a, a second network node 106b, and a third network node 106c. It is understood that the system 100 may comprise any number of network nodes 106. The network nodes 106 may be any of network routers, network switches, media access gateways (MAGs), and other data communication networking equipment. The network nodes 106 may be abstracted as a network cloud or as a communication infrastructure. While the description below refers to the MAT 102, it is understood that at least some of the teachings may be implemented by a desktop computer or other substantially stationary computer that is coupled to the network nodes 106 by a wired connection instead of by a wireless connection.

The base transceiver station 104 may provide a wireless communication link to the MAT 102, providing edge access from the MAT 102 to the network nodes 106, for example to the first network node 106a. The base transceiver station 104 may provide a wireless communication link according to one or more of a code division multiple access (CDMA), a global system for mobile communications (GSM), a long evolution (LTE), a worldwide interoperability for microwave access (WiMAX), or other wireless communication protocol.

In an embodiment, the MAT 102 comprises a radio transceiver 120, a trusted security zone 130, and a secure application 132. For example, the radio transceiver 120 may comprise a cellular communication transceiver that is operable to provide a wireless communication link according to one or more of a code division multiple access (CDMA), a global system for mobile communications (GSM), a long term evolution (LTE), a worldwide interoperability for microwave access (WiMAX), or other wireless communication protocol. The MAT 102 may comprise other radio transceivers in addition to the radio transceiver 120, for example a near field communication (NFC) radio transceiver, a Bluetooth® radio transceiver, a WiFi radio transceiver, or other short range radio transceiver.

As described above, the trusted security zone 130 may be provided by a physically separate processor or by a virtual processor. The secure application 132 may be any of a variety of applications that process and/or transmit confidential information. The confidential information may comprise sensitive business documents such as electronic mail, marketing literature, business plans, client lists, addresses, employee data, intellectual property documents, and the like. The confidential information may comprise personal medical records or medical data that are subject to privacy requirements enforced by government regulatory bodies or commercial standards. The confidential information may comprise financial information such as account numbers, authentication identities, account balance information, and the like.

When processing and/or transmitting the confidential information, the secure application 132 executes at least partially in the trusted security zone 130. It is a characteristic or feature of the trusted security zone 130, as described more fully above, that when the secure application 132 executes in the trusted security zone 130, untrusted applications are prevented from executing and/or accessing trusted memory partitions and/or accessing the display or input devices of the MAT 102, thereby reducing the opportunity for malware that may have infiltrated the MAT 102 to corrupt or to monitor the confidential information. When the confidential information is transmitted by the secure application 132 via a trusted end-to-end communication link to the secure cloudlet 108, the trusted security zone 130 builds a message that comprises the confidential information, which may be referred to as a content portion or a content of the message, and a first trust token. In some contexts, the message may be said to incorporate or to encapsulate the content portion and the first trust token. The first trust token comprises information that may be used by another trusted security zone to verify a trust level of the message. The first trust token may comprise indications or information about how the message was handled, e.g., processed in the trusted security zone 130, and may be viewed as a kind of birth certificate or pedigree of the message. Some or all of the trust token may be encrypted to avoid monitoring or tampering by untrusted nodes. In some contexts, the verification of the trust level of the message by analyzing the trust token or a plurality of trust tokens incorporated in, encapsulated in, or adjoined to a message may be referred to as verifying a continuity of trust of the message and/or verifying a continuity of trust of at least a portion of the trusted end-to-end communication link.

Each of the network nodes 106 comprises a trusted security zone 136. In some contexts, the network nodes 106 may be referred to as trusted network nodes or trusted nodes. The first network node 106a comprises a first trusted security zone 136a, the second network node 106b comprises a second trusted security zone 136b, and the third network node 106c comprises a third trusted security zone 136c. In an embodiment, the network nodes 106 may be dedicated solely to providing trusted end-to-end communication links and may carry no untrusted message traffic. Alternatively, the network nodes 106 may carry both trusted and untrusted message traffic, suspending handling of all untrusted message traffic when handling a trusted message. In an embodiment, communication devices that do not process the message at the network layer of the open system interconnect (OSI) model or above are assumed to be trusted and are not burdened with verifying the continuity of trust of the message before forwarding the message on along the trusted end-to-end communication link.

The Internet protocol is an example of a network layer process, and the transfer control protocol (TCP) is an example of a process that processes messages at a layer above the network layer. Data communication hubs and the base transceiver station 104 are examples of communication devices or nodes that do not process messages at the network layer or above. In another embodiment, however, lower layer communication devices perform some verification of the continuity of trust of the message.

In an embodiment, the processing of a message at one network node 106 at each of a plurality of communication layers at or above the network layer is performed by one or more applications executing at least in part in the trusted security zone 136 of the subject network node 106. For example, if the first network node 106a processes the message at both the IP layer and at the UDP layer, the processing at the IP layer is conducted by an application executing at least in part in the trusted security zone 136a, and the processing of the message at the UDP layer is conducted by an application executing at least in part in the trusted security zone 136a. In an embodiment, a trusted token may be generated and associated with the message by an application processing the message at a first communication layer, and a second trusted token may be generated and associated with the message by an application processing the message at a second communication layer. For example, a first application processing the message at the IP communication layer and executing at least in part in the trusted security zone 136a may generate a first trust token and associate it with the message, and a second application processing the message at the UDP communication layer and executing at least in part in the trusted security zone 136a may generate a second trust token and associate it with the message. In an embodiment, the first and second trust tokens may be generated by a base layer of functionality and/or utilities of the trusted security zone 136a that is invoked by the first and second applications.

When the message is received by the network node 106, the message is identified as a message to be processed by the trusted security zone 136, for example the message may be identified as a trusted message by a field of the message or by the presence of a trust token in the message. The message is analyzed by the trusted security zone 136 to determine the trust level of the message, for example by examining one or more trust tokens that may be encapsulated in the message or associated with the message. If the trust level of the message is sufficient, the network node 106 processes the message, builds a new trust token, encapsulates the new trust token into the message, and sends the message on to the next network node 106 for handling. The message processing, trust token creation, and message transmitting are performed in the trusted security zone 136 of the network node 106. The new trust token comprises information that may be used by another trusted security zone to verify the trust level of the message, for example to verity that the subject network node processed the message in such a manner as to maintain trust continuity of the message.

When the message has transited the trusted end-to-end communication link and is received by the trusted security zone 138 of the server located in the cloud computing facility 110, the trust level of the message is analyzed to determine that the continuity of trust of the message has been maintained and that the trust level of the message is sufficient. In an embodiment, the trust level may be a figure of merit that varies over a range of numerical values, for example from 0 to 1, from 0 to 10, from 1 to 10, from 0 to 100, from 1 to 100 or over some other numerical range. The numerical values may be integer values or decimal values. Alternatively, the trust level may be a binary value, either trusted or untrusted. In another embodiment, some other scale of trust level may be implemented. If the trust level of the message is sufficient, the message is provided to the secure cloudlet 108 executing in the trusted security zone 138, and the secure cloudlet 108 consumes the message. For example, the secure cloudlet 108 may process the message in any of a variety of ways including storing the content of the message in a data store, analyzing the content, aggregating the content with other previously received content, and/or other processing.

The communication infrastructure and processing method described above can be said to provide a trusted end-to-end communication link, because processing of the message at the network layer and above is performed by applications executing at least in part in a trusted security zone that first verifies the continuity of trust of the message before processing it. This infrastructure and processing method promotes a communication end point, for example the secure cloudlet 108, being able to have a high level of confidence that the content of the message has not been intercepted and copied and/or tampered with.

Figure 2:
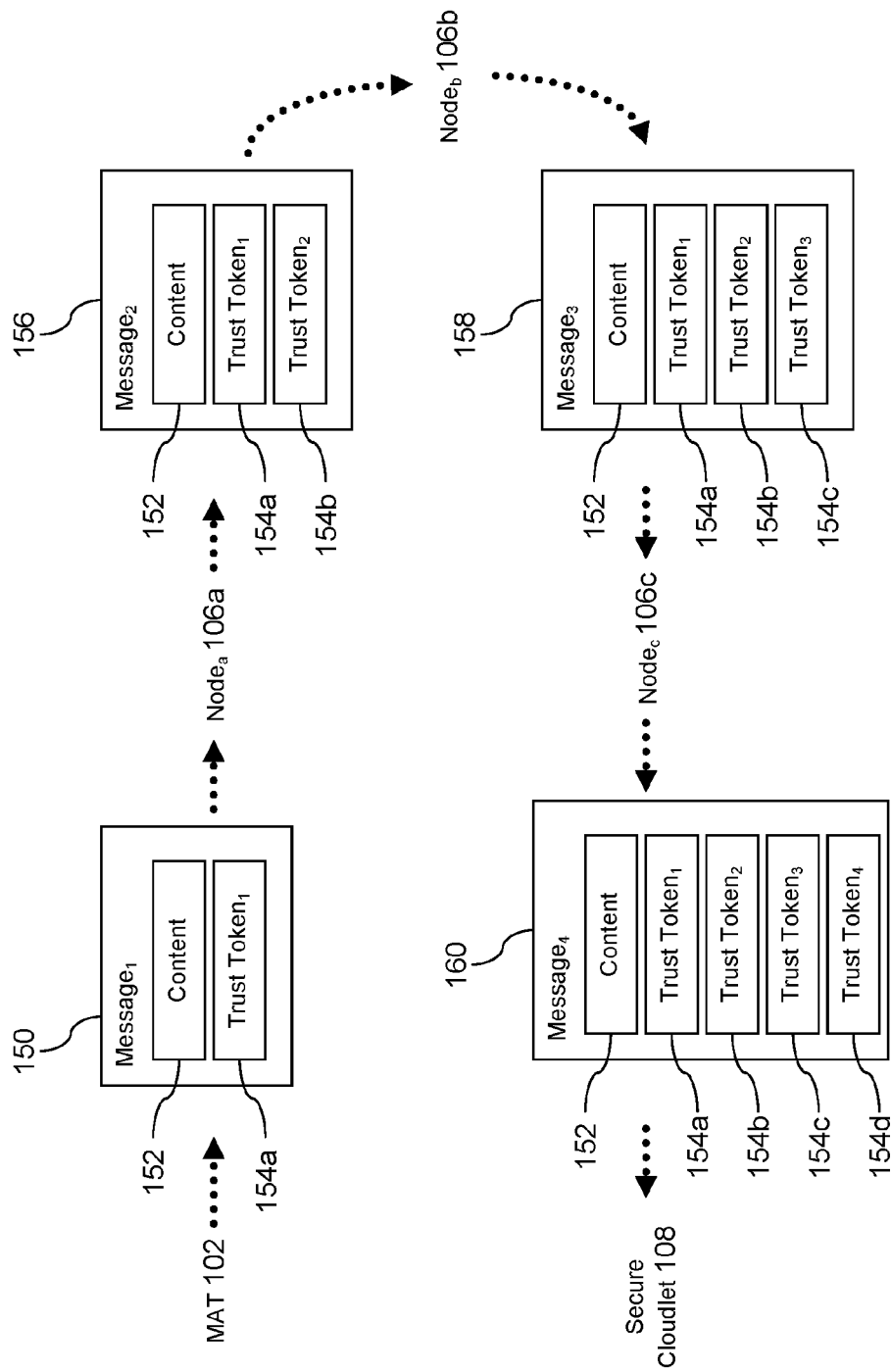
FIG. 2 is an illustration of a message flowing through a trusted end-to-end communication link according to an embodiment of the disclosure.

Turning now to FIG. 2, an example of message propagation through the trusted end-to-end communication link is described. The MAT 102 builds a first message 150 comprising a content 152 and a first trust token 154a. For example, the trusted security zone 130 and/or the secure application 132 executing in the trusted security zone 130 creates the content 152, builds the first trust token 154a, and composes the first message 150 from the content 152 and the first trust token 154a. As described above, trust tokens may comprise information that may be used by another trusted security zone to verify the trust level of the message. Trust tokens may be analogized to a birth certificate and/or a pedigree. The trust token may comprise encrypted data and/or identity codes that can be decrypted by a trusted security zone to assure that the sending network element has maintained the continuity of trust of the message. The identity codes may identify a network node 136 or other communication device in the path of the trusted end-to-end communication link. The MAT 102 and/or the trusted security zone 130 transmits the first message 150 to the first node 106a.

The first node 106a processes the first message 150 in the first trusted security zone 136a by analyzing the first message 150 to verify the continuity of trust of the first message 150. For example, the first trusted security zone 136a, or a secure communication application executing in the first trusted security zone 136a, reads and validates the first trust token 154a, which may be referred to as verifying the continuity of trust of the first message 150. In an embodiment, the first trusted security zone 136a may determine a trust level of the first message 150. If the first message 150 has an acceptable trust level, the first trusted security zone 136a builds a second trust token 154b and composes a second message 156 from the content 152, the first trust token 154a, and the second trust token 154b. Alternatively, the second message 156 may not comprise the first trust token 154a, and the second trust token 154b may comprise information about the level of trust determined by the first trusted security zone 136a when verifying the continuity of trust of the first message 150. The first network node 106a and/or the first trusted security zone 136a transmits the second message 156 to the second network node 106b.

The second network node 106b processes the second message 156 in the second trusted security zone 136b by analyzing the second message 156 to verify the continuity of trust of the second message 156, builds a third trust token 154c, and builds a third message 158 comprising the first trust token 154a, the second trust token 154b, and the third trust token 154c. Alternatively, only the third trust token 154c is encapsulated in the third message 158, and information about the level of trust associated with the first message 150 determined by the first network node 106a and the level of trust associated with the second message 156 determined by the second network node 106b is included in the third trust token 154c. The second network node 106b and/or the second trusted security zone 136b transmits the third message 158 to the third network node 106c.

The third network node 106c processes the third message 158, builds a fourth message 160 including a fourth trust token 154d in a similar fashion, and transmits the fourth message 160 to the trusted security zone 138 and/or the secure cloudlet 108. While the propagation of the content 152 through the trusted end-to-end communication link has been described by speaking of a plurality of different but related messages—a first message 150, a second message 156, a third message 158, and a fourth message 160—according to a different manner of speaking or a different abstraction it could be said that one message propagates through the trusted end-to-end communication link, where the one message is extended or progressively composed in its transit of the link. In an embodiment, rather than a trust token or trust tokens being encapsulated in the messages 150, 156, 158, 160, the trust token and/or trust tokens may be linked to the messages 150, 156, 158, 160, such as being linked by being contained within a single payload of an IP packet.

Each of the messages 150, 156, 158, and 160 may be encapsulated as a payload of a data packet, for example as a payload of an IP packet or an IP datagram. Depending on the size of the content 152 and the one or more trust tokens 154, the content 152 may be segmented into multiple segments and each segment sent separately in a message as described above. It is understood that the trusted end-to-end communication link may comprise any number of network nodes 106 and that any number of corresponding messages may be built in communicating the content 152 from the MAT 102 to the secure cloudlet 108.

Figure 3A:
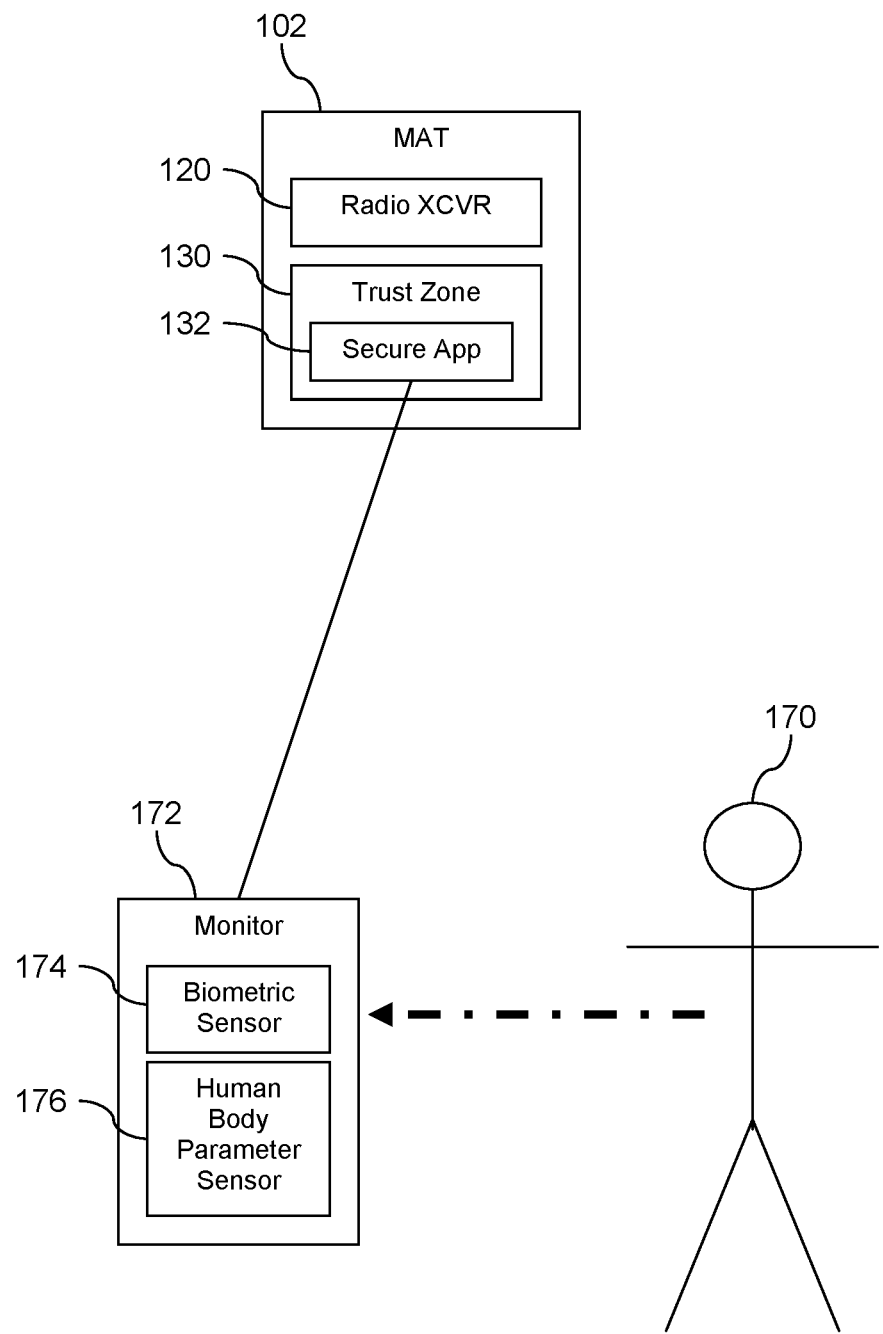
FIG. 3A is an illustration of a human body monitor according to an embodiment of the disclosure.
Figure 3B:
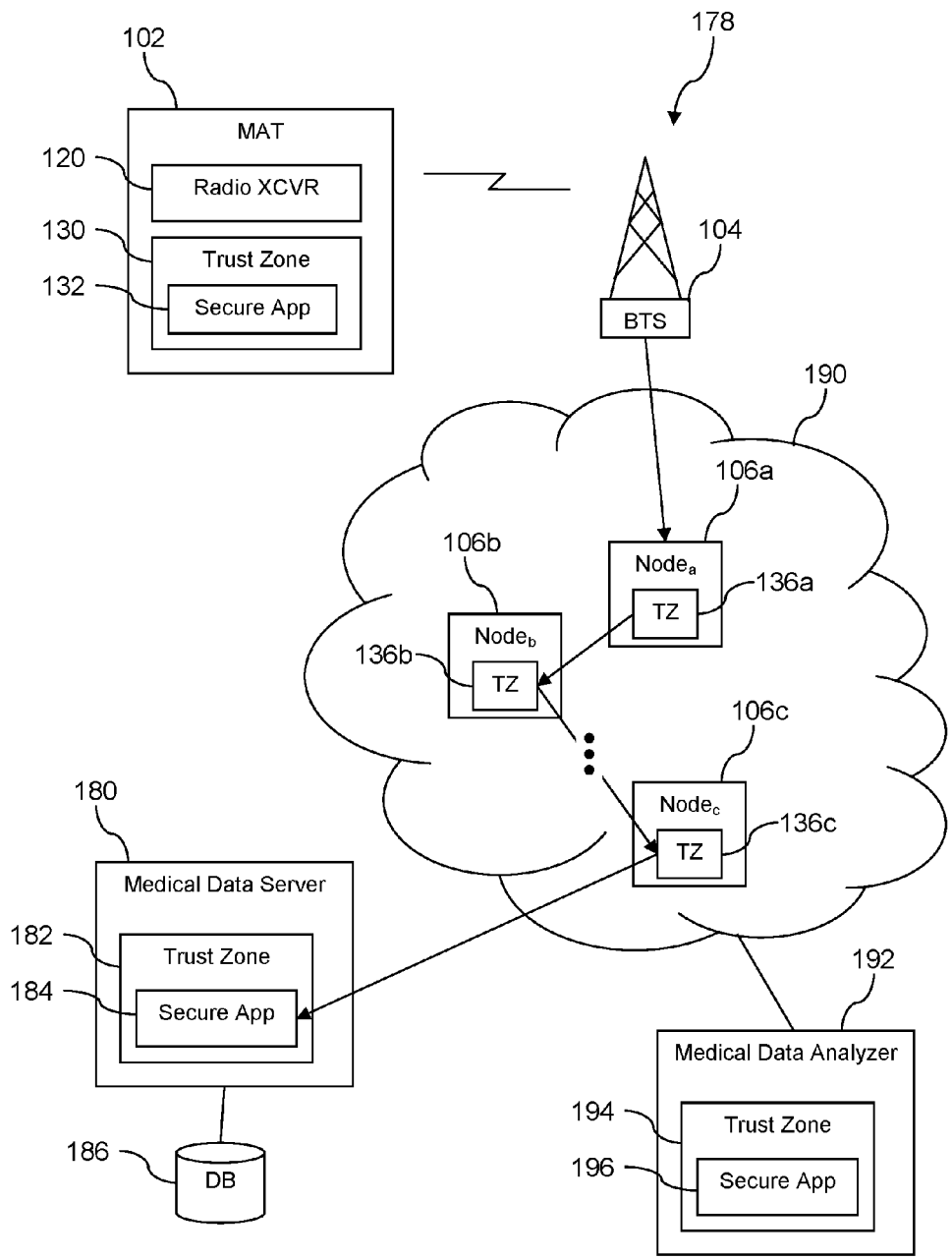
FIG. 3B is an illustration of a system for delivery of medical information according to an embodiment of the disclosure.

Turning now to FIG. 3A and FIG. 3B, a monitor 172 and a second system 178 for providing trusted end-to-end communication links is described. In an embodiment, the monitor 172 comprises a biometric sensor 174 and a human body parameter sensor 176. The trusted network nodes 106a, 106b, 106c may be abstracted to be parts of a network 190. Network 190 may comprise additional nodes and/or communication devices and may comprise one or more public networks, private networks, or a combination thereof. The body parameter sensor 176 may measure or sample a bodily parameter of a human being 170 such as a blood sugar level, a blood thickness, a blood pressure, a bodily temperature, a blood oxygen saturation level, a pulse rate, a heart rhythm, or another bodily parameter. In some contexts the body parameter sensor 176 may be referred to as a transducer or as comprising a transducer. The body parameter sensor 176 may capture only raw data values that may not be directly related to a standard measurement value, and the raw data values may be processed by another device, for example processed by the secure application 132 executing in the trusted security zone 130 of the MAT 102, to represent the value of the sensed parameter in standard or customary units. For example the secure application 132 may process blood thickness raw data received from the monitor 172 and/or the body parameter sensor 176 to determine an international normalized ratio (INR) value of blood thickness based on the raw data. Alternatively, the body parameter sensor 176 and/or the monitor 172 may process the raw data and output these bodily parameter values in standard units.

The biometric sensor 174 captures a biometric signature of the human being 170, for example a finger print, a retinal scan, a face scan, a DNA signature, or other biometric signature. In some contexts, the biometric sensor 174 may be referred to as a biometric scanner. In an embodiment, the biometric sensor 174 and the body parameter sensor 176 may capture a biometric signature and a body parameter value substantially concurrently. In an embodiment, the monitor 172 may be configured such that the process of sensing the body parameter value by the body parameter sensor 176 and of capturing the biometric signature by the biometric sensor 174 are inseparable processes. For example, in an embodiment, the body parameter sensor 176 and the biometric sensor 174 are integrated into a single package such as a pulse oximeter clamp that also captures a finger print biometric. As is known by those skilled in the art, a standard oximeter clamp may be clamped to a finger to read both a pulse rate and a blood oxygen saturation percentage. The biometric signature may be associated with the body parameter value to identify and/or corroborate the identity of the human being 170.

The monitor 172 may be communicatively coupled to the MAT 102, for example via a wired communication link or via a short range wireless communication link such as NFC, Bluetooth®, or WiFi wireless links. The monitor 172 transmits the body parameter value and the biometric signature to the secure application 132 executing in the trusted security zone 130 of the MAT 102. The communication from the monitor 172 to the MAT 102 is assumed to be trusted and/or substantially invulnerable to hacking. The secure application 132 may produce a medical record content that comprises the body parameter value and the biometric signature. The biometric signature may be encoded and/or compressed in one or more ways and may be encapsulated in the medical record content in the form of a pleogram. In an embodiment, the medical record content may comprise additional supporting information such as a date and a time of day. The secure application 132 may create a message comprising the medical record content and a trust token and send the message over a trusted end-to-end communication link to a secure application 184 executing in a trusted security zone 182 of a medical data server 180. The propagation of the message over the trusted end-to-end communication link may be substantially similarly to the process described above.

The secure application 184 may provide for storing the medical record content in a data store 186 coupled to the medical data server 180. The secure application 184, or a different secure application executing in the trust zone 182 of the medical data server 180, may process a plurality of medical record contents of a single human being 170 to track a chronic condition of the human 170. Alternatively, the secure application 184 may process a plurality of medical record contents associated with a plurality of selected humans 170, for example to calculate an efficacy of a medical treatment or drug.

In an embodiment, a secure application 196 executing in a trusted security zone 194 of a medical data analyzer 192 requests medical record contents from the medical data server 180, and the medical data server 180 sends the requested medical record contents via a trusted end-to-end communication link as described above. The medical records may be said to be verifiably confidential medical records. In some circumstances, regulatory agencies, such as the FDA, may inspect the use and communication of medical records to confirm the compliance with medical record privacy regulations. The secure application 196 may analyze the medical record contents to diagnose a condition of the human 170 and/or to recommend a medical treatment program for the human. A medical doctor using the medical data analyzer 192, for example, may write a prescription for the human being 170 and send the prescription to a pharmacy that is customarily used by the human being 170. The secure application 196 may analyze medical records of a plurality of humans 170 to determine an efficacy of a medical treatment or drug.

Figure 4:
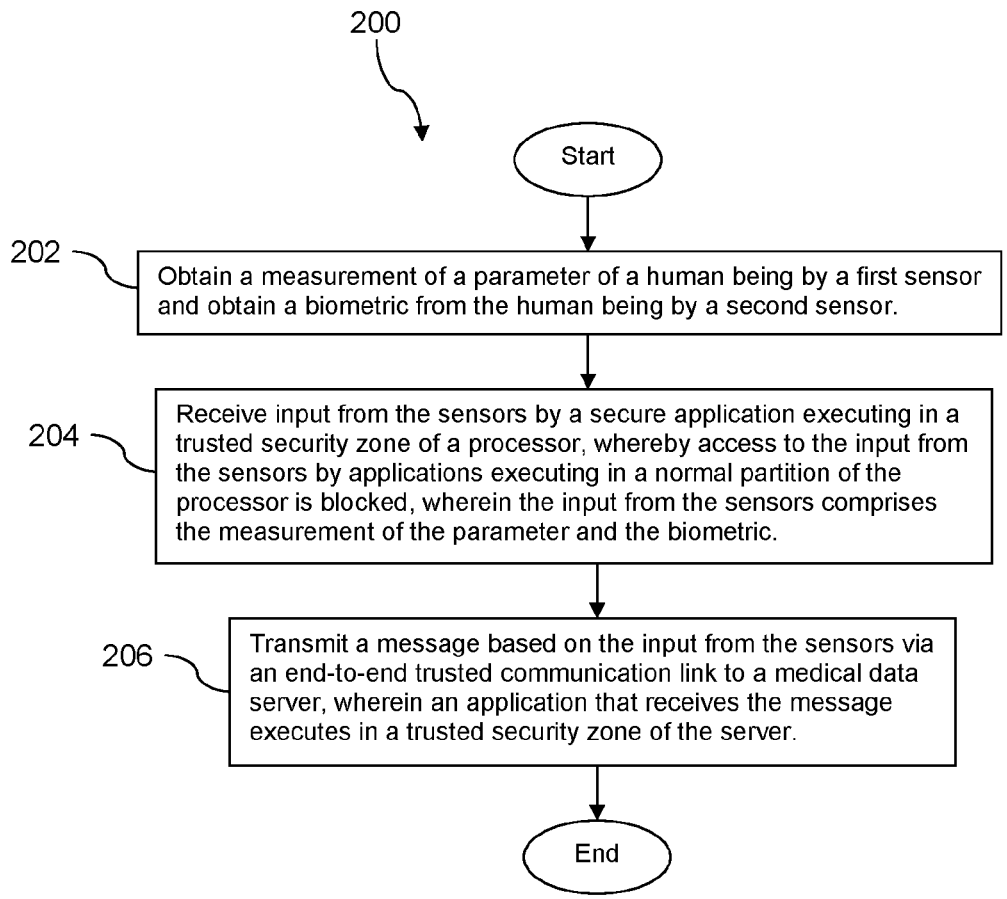
FIG. 4 is a flow chart of a method according to an embodiment of the disclosure.

Turning now to FIG. 4, a method 200 is described. At block 202, a measurement of a parameter of a human being is obtained by a first sensor and a biometric of the human being is obtained by a second sensor. For example, a parameter of a human being is obtained by the body parameter sensor 176 and a biometric signature of the human being is obtained by the biometric sensor 174 as described above. At block 204, input from the sensors is received by a secure application executing in a trusted security zone of a processor, whereby access to the input from the sensors by applications executing in a normal partition of the processor is blocked, wherein the input from the sensors comprise the measurement of the parameter of the human being and the biometric of the human being. At block 206, a message based on the input from the sensors is transmitted via a trusted end-to-end communication link to a medical data server, wherein an application that receives the message executes in a trusted security zone of the server. The message may be substantially similar to the first message 150 described above and may comprise a content portion and one or more trust tokens.

Figure 5:
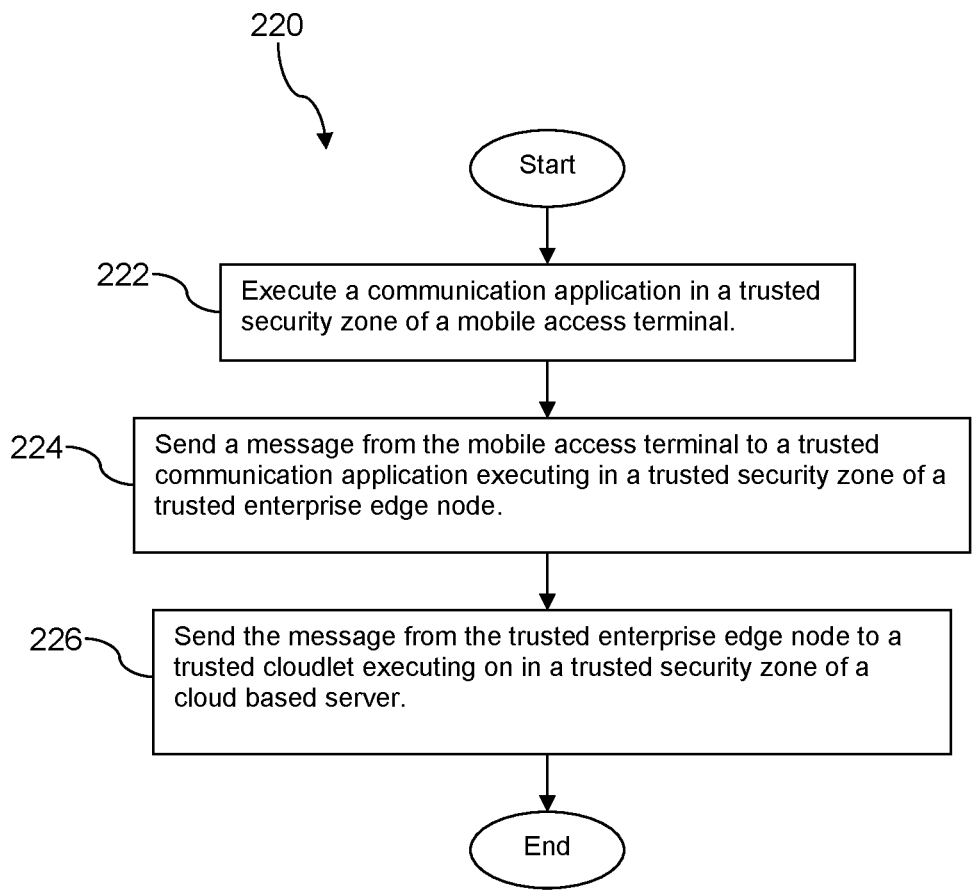
FIG. 5 is a flow chart of another method according to an embodiment of the disclosure.

Turning now to FIG. 5, a method 220 is described. At block 222, a communication application is executed in a trusted security zone of a mobile access terminal. For example, the secure application 132 executes in the trusted security zone 130 of the MAT 102 as described above. At block 224, a message is sent from the mobile access terminal to a trusted communication application executing in a trusted security zone of a trusted enterprise edge node. For example, the secure application 132 and/or the trusted security zone 130 builds the message 150 comprising the content 152 and the trust token 154 and sends the message 150 to the first network node 106a. In an embodiment, the message may be sent from the MAT 102 to an enterprise communication network via a virtual private network (VPN) session. The message may be directed to a device or service outside the enterprise communication network and may then propagate in the external Internet. The first network node 106a may be an enterprise firewall or a multi-protocol label switching port of a router. Thus, in this embodiment the enterprise network edge may have a trusted security zone to support a trusted end-to-end communication link from the enterprise network to external devices and/or external functionalities. At block 226, the message is sent from the trusted enterprise edge node to a trusted cloudlet executing on a trusted security zone of a cloud based server according to the processes for providing continuity of trust in the propagation of the message described above.

Figure 6:
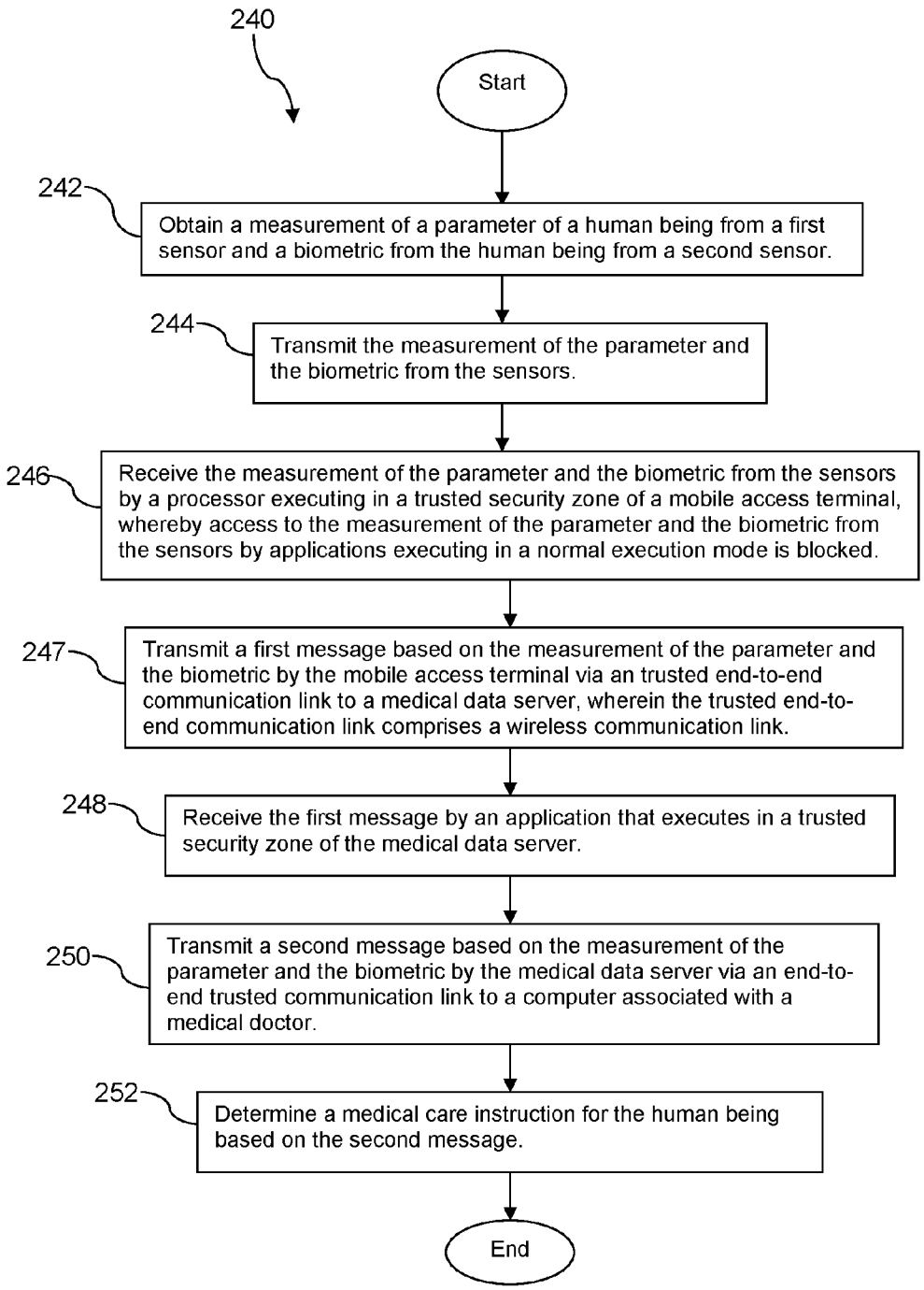
FIG. 6 is a flow chart of another method according to an embodiment of the disclosure.

Turning now to FIG. 6, a method 240 is described. At block 242, a measurement of a parameter of a human being is obtained by a first sensor and a biometric from the human being is obtained by a second sensor. For example, the body parameter sensor 176 obtains a parameter value, and the biometric sensor 174 obtains a biometric signature from the human 170. At block 244, the measurement of the parameter and the biometric signature is transmitted from the sensors, for example the parameter value and the biometric signature are transmitted by the monitor 172 to the MAT 102. At block 246, the measurement of the parameter and the biometric signature are received by a processor executing in a trusted security zone of a mobile access terminal from the sensors, whereby access to the measurement of the parameter and the biometric from the sensors by applications executing in a normal execution mode is blocked. For example, the parameter and the biometric signature are received by the secure application 132 executing in the trusted security zone 130 of the MAT 102.

At block 247, a first message is transmitted based on the measurement of the parameter and the biometric by the mobile access terminal via an trusted end-to-end communication link to a medical data server, wherein the trusted end-to-end communication link comprises a wireless communication link. For example, the first message is the first message 150 and the wireless communication link is established between the radio transceiver 120 and the base transceiver station 104.

At block 248, the first message is received by an application that executes in a trusted security zone of the medical data server. At block 250, a second message based on the measurement of the parameter and the biometric is transmitted by the medical data server via an end-to-end trusted communication link to a computer associated with a medical doctor. At block 252, a medical care instruction for the human being is determined based on the second message. For example, a medical doctor using the medical data analyzer 192 diagnoses a condition or status of the human 170 and prescribes a medication to treat the condition or status.

Figure 7:
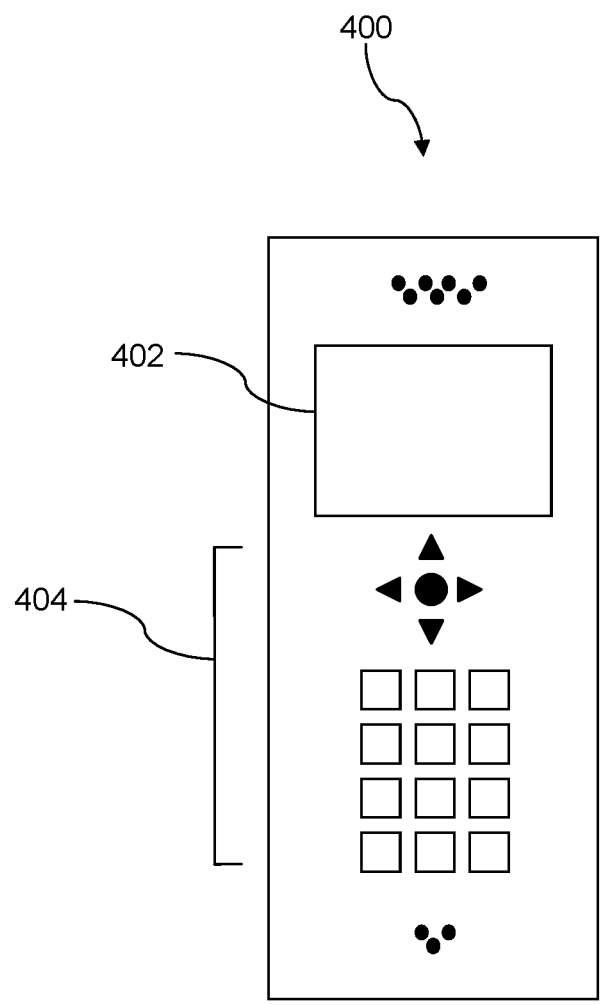
FIG. 7 is an illustration of a mobile access terminal according to an embodiment of the disclosure.

FIG. 7 shows a wireless communications system including a mobile device 400. FIG. 4 depicts the mobile device 400, which is operable for implementing aspects of the present disclosure, but the present disclosure should not be limited to these implementations. In an embodiment, the mobile access terminal 102 may be implemented as the mobile device 400. Though illustrated as a mobile phone, the mobile device 400 may take various forms including a wireless handset, a pager, a personal digital assistant (PDA), a gaming device, or a media player. The mobile device 400 includes a display 402 and a touch-sensitive surface and/or keys 404 for input by a user. The mobile device 400 may present options for the user to select, controls for the user to actuate, and/or cursors or other indicators for the user to direct. The mobile device 400 may further accept data entry from the user, including numbers to dial or various parameter values for configuring the operation of the handset. The mobile device 400 may further execute one or more software or firmware applications in response to user commands. These applications may configure the mobile device 400 to perform various customized functions in response to user interaction. Additionally, the mobile device 400 may be programmed and/or configured over-the-air, for example from a wireless base station, a wireless access point, or a peer mobile device 400. The mobile device 400 may execute a web browser application which enables the display 402 to show a web page. The web page may be obtained via wireless communications with a base transceiver station, a wireless network access node, a peer mobile device 400 or any other wireless communication network or system.

Figure 8:
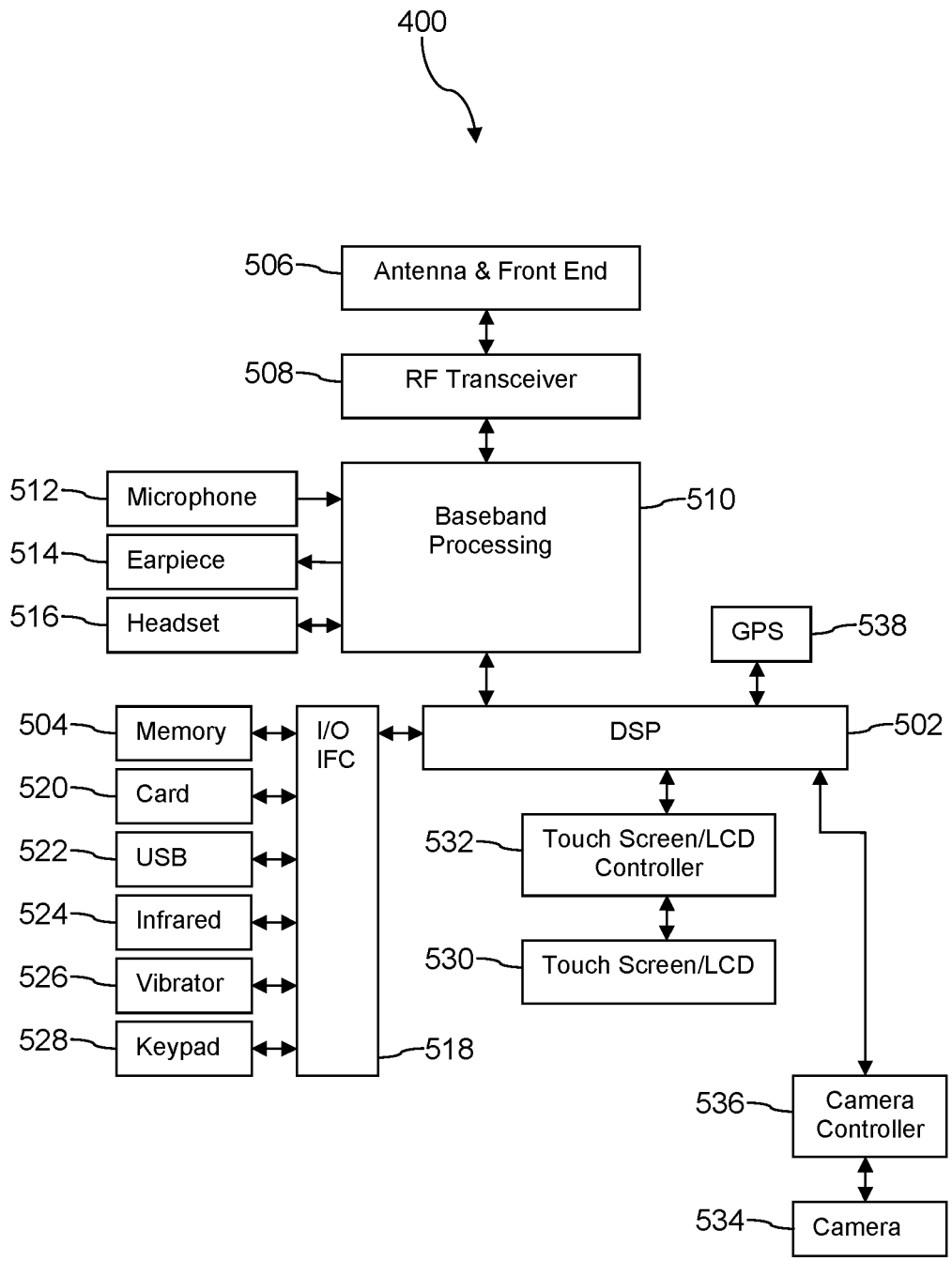
FIG. 8 is a block diagram of a mobile access terminal according to an embodiment of the disclosure.

FIG. 8 shows a block diagram of the mobile device 400. While a variety of known components of handsets are depicted, in an embodiment a subset of the listed components and/or additional components not listed may be included in the mobile device 400. The mobile device 400 includes a digital signal processor (DSP) 502 and a memory 504. As shown, the mobile device 400 may further include an antenna and front end unit 506, a radio frequency (RF) transceiver 508, a baseband processing unit 510, a microphone 512, an earpiece speaker 514, a headset port 516, an input/output interface 518, a removable memory card 520, a universal serial bus (USB) port 522, an infrared port 524, a vibrator 526, a keypad 528, a touch screen liquid crystal display (LCD) with a touch sensitive surface 530, a touch screen/LCD controller 532, a camera 534, a camera controller 536, and a global positioning system (GPS) receiver 538. In an embodiment, the mobile device 400 may include another kind of display that does not provide a touch sensitive screen. In an embodiment, the DSP 502 may communicate directly with the memory 504 without passing through the input/output interface 518. Additionally, in an embodiment, the mobile device 400 may comprise other peripheral devices that provide other functionality.

The DSP 502 or some other form of controller or central processing unit operates to control the various components of the mobile device 400 in accordance with embedded software or firmware stored in memory 504 or stored in memory contained within the DSP 502 itself. In addition to the embedded software or firmware, the DSP 502 may execute other applications stored in the memory 504 or made available via information carrier media such as portable data storage media like the removable memory card 520 or via wired or wireless network communications. The application software may comprise a compiled set of machine-readable instructions that configure the DSP 502 to provide the desired functionality, or the application software may be high-level software instructions to be processed by an interpreter or compiler to indirectly configure the DSP 502.

The DSP 502 may communicate with a wireless network via the analog baseband processing unit 510. In some embodiments, the communication may provide Internet connectivity, enabling a user to gain access to content on the Internet and to send and receive e-mail or text messages. The input/output interface 518 interconnects the DSP 502 and various memories and interfaces. The memory 504 and the removable memory card 520 may provide software and data to configure the operation of the DSP 502. Among the interfaces may be the USB port 522 and the infrared port 524. The USB port 522 may enable the mobile device 400 to function as a peripheral device to exchange information with a personal computer or other computer system. The infrared port 524 and other optional ports such as a Bluetooth® interface or an IEEE 802.11 compliant wireless interface may enable the mobile device 400 to communicate wirelessly with other nearby handsets and/or wireless base stations.

The keypad 528 couples to the DSP 502 via the interface 518 to provide one mechanism for the user to make selections, enter information, and otherwise provide input to the mobile device 400. Another input mechanism may be the touch screen LCD 530, which may also display text and/or graphics to the user. The touch screen LCD controller 532 couples the DSP 502 to the touch screen LCD 530. The GPS receiver 538 is coupled to the DSP 502 to decode global positioning system signals, thereby enabling the mobile device 400 to determine its position.

Figure 9A:
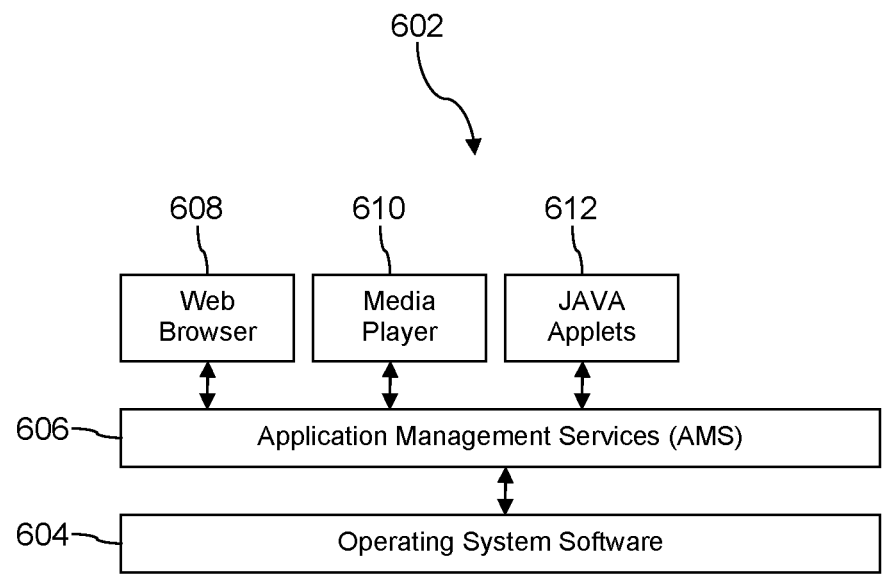
FIG. 9A is an illustration of a software architecture according to an embodiment of the disclosure.

FIG. 9A illustrates a software environment 602 that may be implemented by the DSP 502. The DSP 502 executes operating system software 604 that provides a platform from which the rest of the software operates. The operating system software 604 may provide a variety of drivers for the handset hardware with standardized interfaces that are accessible to application software. The operating system software 604 may be coupled to and interact with application management services (AMS) 606 that transfer control between applications running on the mobile device 400. Also shown in FIG. 9A are a web browser application 608, a media player application 610, and JAVA applets 612. The web browser application 608 may be executed by the mobile device 400 to browse content and/or the Internet, for example when the mobile device 400 is coupled to a network via a wireless link. The web browser application 608 may permit a user to enter information into forms and select links to retrieve and view web pages. The media player application 610 may be executed by the mobile device 400 to play audio or audiovisual media. The JAVA applets 612 may be executed by the mobile device 400 to provide a variety of functionality including games, utilities, and other functionality.

Figure 9B:
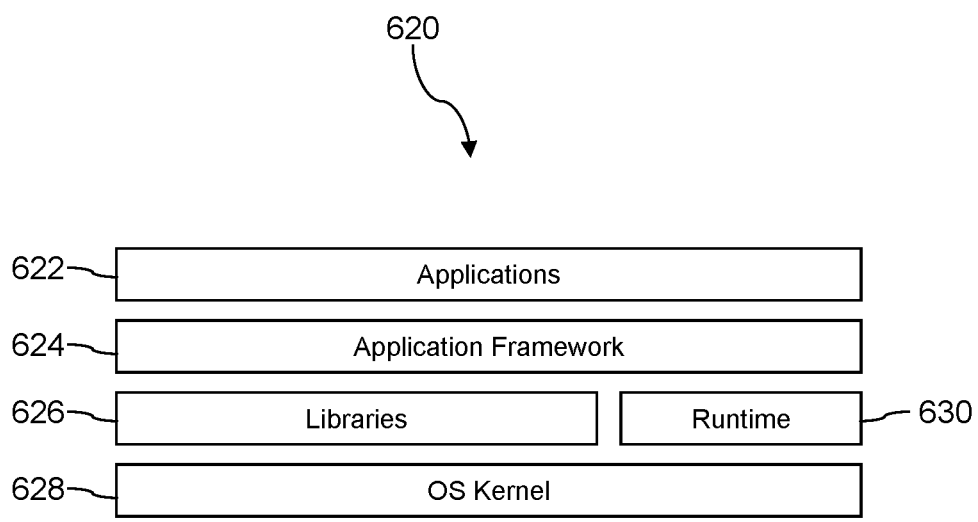
FIG. 9B is an illustration of another software architecture according to an embodiment of the disclosure.

FIG. 9B illustrates an alternative software environment 620 that may be implemented by the DSP 502. The DSP 502 executes operating system software 628 and an execution runtime 630. The DSP 502 executes applications 622 that may execute in the execution runtime 630 and may rely upon services provided by the application framework 624. Applications 622 and the application framework 624 may rely upon functionality provided via the libraries 626.

Figure 10:
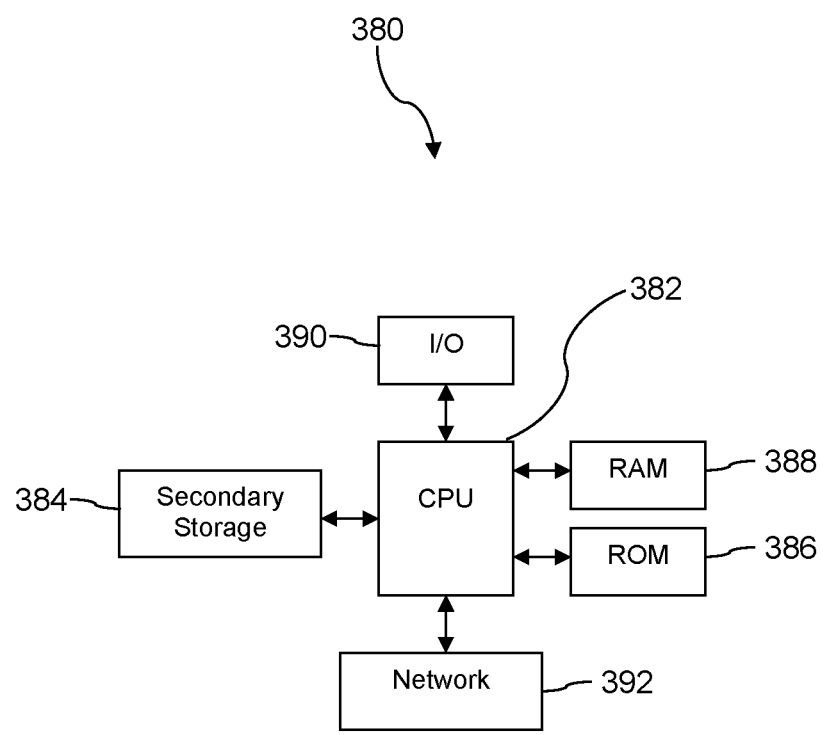
FIG. 10 is a block diagram of a computer system according to an embodiment of the disclosure.

FIG. 10 illustrates a computer system 380 suitable for implementing one or more embodiments disclosed herein. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), $4^{th}$ generation, $5^{th}$ generation, and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embedded in a carrier wave. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method establishing a trusted end-to-end communication link to provide secure access to information, the method comprising:

receiving an input by a processor executing in a trusted security zone of a mobile access terminal, wherein the trusted security zone includes a hardware root of trust and a secure partition that receives the input;

preventing, by execution of the processor in the trusted security zone, applications outside of the trusted security zone from executing on the mobile access terminal, wherein applications that execute outside of the trusted security zone are blocked from accessing the secure partition that received the input;

generating, by a secure application stored in the secure partition and executing on the processor in the trusted security zone of the mobile access terminal, a message and a trust token for transmission via a trusted end-to-end communication link, wherein the trusted end-to-end communication link comprises a plurality of network nodes and provides handling of the message in a corresponding trusted security zone of each network node along the trusted end-to-end communication link; and transmitting, by the mobile access terminal, the message and trust token along the trusted end-to-end communication link to a trusted cloudlet executing in a trusted security zone of a cloud based server, wherein the cloud based server is one endpoint in the trusted end-to-end communication link with the mobile access terminal.

2. The method of claim 1, wherein the trust token is associated with the trusted security zone of the mobile access terminal.

3. The method of claim 1, wherein the trust token is verified by a trusted security zone of each network node in the trusted end-to-end communication link prior to being received by the cloud based server, and wherein the trust token validates the trust level of the trusted end-to-end communication link.

4. The method of claim 1, wherein the trust token is encapsulated within the message prior to transmitting the message to the cloud based server via the trusted end-to-end communication link.

5. The method of claim 1, wherein the trust token is comprised within or appended to the message prior to the transmitting.

6. The method of claim 5, wherein each trusted security zone disables execution of applications, that are outside the trusted security zone, during execution of the trusted security zone.

7. The method of claim 6, wherein each trusted security zone comprises at least one of a virtual processor, a physical processor, or a combination thereof.

8. A method establishing a trusted end-to-end communication link to provide secure access to information, the method comprising:

receiving, by a trusted cloudlet executing in a trusted security zone of a cloud based server, a message and a trust token sent from a mobile access terminal;

determining, by the trusted cloudlet while preventing execution of applications that execute outside of the trusted security zone of the cloud based server, that the message was generated in a trusted security zone of the mobile access terminal based on the trust token;

verifying, by the trusted cloudlet in the trusted security zone of the cloud based server, that the message was handled in trusted security zones along a trusted end-to-end communication link, wherein each trusted security zone includes a hardware root of trust and a secure partition; and based on the verification, executing the message in the trusted security zone of the cloud based server while preventing execution of applications that execute outside of the trusted security zone of the cloud based server.

9. The method of claim 8, wherein executing the message in the trusted security zone of the cloud based server maintains continuity of the trusted end-to-end communication link.

10. The method of claim 8, wherein the trusted end-to-end communication link comprises a plurality of network nodes that each handle the message in a corresponding trusted security zone.

11. The method of claim 10, wherein each of the plurality of network nodes generate an additional trust token or append the trust token generated in the trusted security zone of the mobile access terminal.

12. The method of claim 8, further comprising: prior to receiving the message by the trusted cloudlet in the trusted security zone of the cloud based server, responding to a request from a network node of the trusted end-to-end communication link to validate a trusted status of the cloud based server.

13. The method of claim 8, wherein each trusted security zone comprises at least one of a virtual processor, a physical processor, or a combination thereof.

14. A method establishing a trusted end-to-end communication link to provide secure access to information, the method comprising:
   receiving, by a trusted communication application executing in a trusted security zone of a trusted enterprise edge node, a message via a trusted end-to-end communication link from a communication application executing in a trusted security zone of a mobile access terminal;
   determining, by the trusted communication application of the trusted enterprise edge node while preventing execution of applications that execute outside of the trusted security zone of the trusted enterprise edge node, that the message was handled in the trusted security zone of the mobile access terminal, wherein each trusted security zone includes a hardware root of trust and a secure partition; and
   in response to the determining, sending the message, from the trusted security zone of the trusted enterprise edge node, to a trusted cloudlet executing in a trusted security zone of a cloud based server, wherein sending the message to the trusted security zone of the cloud based server maintains continuity of the trusted end-to-end communication link.

15. The method of claim 14, wherein the trusted enterprise edge node comprises at least one of a firewall server or a multi-protocol label switching (MPLS) port on a router.

16. The method of claim 14, wherein the trusted security zone of the trusted enterprise edge node includes a processor blocking applications executing in a normal partition outside of the trusted security zone from accessing memory, reading inputs, and writing outputs while the trusted communication application executes in the trusted security zone of the trusted enterprise edge node.

17. The method of claim 14, wherein the trusted security zone of the trusted enterprise edge node is provided by a first virtual processor, and wherein a normal partition of the trusted enterprise edge node is provided by a second virtual processor, and while the first virtual processor is executing, the second virtual processor does not execute instructions.

18. The method of claim 14, wherein at least one trust token is included with the message sent from the trusted security zone of the mobile access terminal via the trusted end-to-end communication link.

19. The method of claim 18, wherein a portion of the trusted end-to-end communication link comprises a cellular wireless communication link.

20. The method of claim 19, wherein the cellular wireless communication link is provided based on at least one of a code division multiple access (CDMA) protocol, a global system for mobile communication (GSM) protocol, a long-term evolution (LTE) protocol, or a worldwide interoperability for microwave access (WiMAX) communication protocol.

* * * * *